US009841418B2

(12) United States Patent
Hanashi

(10) Patent No.: US 9,841,418 B2
(45) Date of Patent: Dec. 12, 2017

(54) METHOD FOR DETECTING TARGET PARTICLE

(71) Applicant: OLYMPUS CORPORATION, Tokyo (JP)

(72) Inventor: Takuya Hanashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 803 days.

(21) Appl. No.: 14/179,174

(22) Filed: Feb. 12, 2014

(65) Prior Publication Data

US 2014/0162378 A1 Jun. 12, 2014

Related U.S. Application Data

(63) Continuation of application No. PCT/JP2012/066576, filed on Jun. 28, 2012.

(30) Foreign Application Priority Data

Aug. 30, 2011 (JP) .................................. 2011-187600

(51) Int. Cl.
| | |
|---|---|
| *G01N 33/543* | (2006.01) |
| *G01N 21/64* | (2006.01) |
| *G02B 21/00* | (2006.01) |
| *G02B 21/26* | (2006.01) |
| *G01N 15/14* | (2006.01) |

(52) U.S. Cl.
CPC ......... *G01N 33/543* (2013.01); *G01N 21/645* (2013.01); *G01N 21/6408* (2013.01); *G01N 21/6428* (2013.01); *G01N 21/6452* (2013.01); *G01N 21/6458* (2013.01); *G01N 33/54326* (2013.01); *G02B 21/0032* (2013.01); *G02B 21/0076* (2013.01); *G02B 21/26* (2013.01); *G01N 15/1456* (2013.01); *G01N 2021/6432* (2013.01); *G01N 2021/6439* (2013.01); *G01N 2021/6441* (2013.01); *G02B 21/0048* (2013.01)

(58) Field of Classification Search
CPC ............. G01N 33/543; G01N 21/6408; G01N 21/6428; G01N 21/645; G01N 21/6452; G01N 33/54326; G01N 15/1456; G01N 2021/6432; G01N 2021/6439; G01N 2021/6441; G02B 21/0032; G02B 21/0076; G02B 21/26; G02B 21/0048
See application file for complete search history.

(56) References Cited

U.S. PATENT DOCUMENTS

| | | | |
|---|---|---|---|
| 4,251,733 A | 2/1981 | Hirleman, Jr. | |
| 4,421,860 A | 12/1983 | Elings et al. | |
| 4,745,077 A * | 5/1988 | Holian ............. | G01N 33/54333 252/62.51 R |
| 4,979,824 A | 12/1990 | Mathies et al. | |
| 5,308,990 A | 5/1994 | Takahashi et al. | |
| 5,547,849 A | 8/1996 | Baer et al. | |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,495,676 B1 | 12/2002 | Wood et al. | |
| 6,563,583 B2 | 5/2003 | Ortyn et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 8,284,484 B2 | 10/2012 | Hoult et al. | |
| 2001/0035954 A1 | 11/2001 | Rahn et al. | |
| 2002/0008211 A1 | 1/2002 | Kask | |

(Continued)

FOREIGN PATENT DOCUMENTS

| | | |
|---|---|---|
| CN | 103620389 A | 3/2014 |
| EP | 1 906 172 A1 | 4/2008 |

(Continued)

OTHER PUBLICATIONS

Nie et al., Real-Time Detection of Single Molecules in Solution by Confocal Flurescence Microscopy, Anal Chem. 1995, 67, pp. 2849-2857.*
Enderlein et al., Optimal Algorithm for Single-Molecule Identification with Time-Correlated Single-Photon Counting, J. Phys. Chem. A 2001, 105, pp. 48-53.*
Yan et al., Simultaneous Enantiomeric Determination of Dansyl-D,L-Phenylalanine by Fluorescence Spectroscopy in the Presence of a-Acid Glycoprotein, Anal. Chem. 1999, 71, pp. 1958-1962.*
U.S. Non-Final Office Action dated Mar. 4, 2015, issued in U.S. Appl. No. 14/172,295. (39 pages).
Communication pursuant to Article 94(3) dated May 13, 2015, issued in European Patent Application No. 11 812 369.4 (5 pages).
Office Action dated Mar. 25, 2015, issued in Chinese Patent Application No. 201180036710.4, with English translation (8 pages).
Advisory Action dated Jan. 5, 2016, issued in U.S. Appl. No. 14/172,295.

(Continued)

*Primary Examiner* — Gary W Counts
(74) *Attorney, Agent, or Firm* — Westerman, Hattori, Daniels & Adrian, LLP

(57) ABSTRACT

This method for detecting a target particle comprises (a) preparing a solution containing a target particle, a luminescent probe that binds to the target particle and a particle for separation and recovery, or containing the target particle bound to the luminescent probe, the luminescent probe and the particle for separation and recovery, and forming a complex composed of the target particle, the luminescent probe and the particle for separation and recovery in the solution, (b) recovering the particle for separation and recovery from the solution by solid-liquid separation treatment after the (a) and preparing a sample solution containing the particle for separation and recovery, and (c) calculating the number of the complex present in the sample solution according to a scanning molecule counting method, wherein the particles for separation and recovery bind to a complex composed of the target particles and the luminescent probe.

9 Claims, 9 Drawing Sheets

(56) References Cited

U.S. PATENT DOCUMENTS

| | | |
|---|---|---|
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2004/0152118 A1 | 8/2004 | Van Atta et al. |
| 2005/0260660 A1 | 11/2005 | van Dongen et al. |
| 2005/0277134 A1 | 12/2005 | Okano et al. |
| 2006/0008799 A1 | 1/2006 | Cai et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2007/0070496 A1* | 3/2007 | Gweon ............... G02B 21/0068 359/386 |
| 2007/0231808 A1 | 10/2007 | Gouda et al. |
| 2007/0250274 A1 | 10/2007 | Volkov et al. |
| 2008/0052009 A1 | 2/2008 | Chiu et al. |
| 2008/0158561 A1 | 7/2008 | Vacca et al. |
| 2009/0159812 A1 | 6/2009 | Livingston |
| 2010/0033718 A1 | 2/2010 | Tanaami |
| 2010/0177190 A1 | 7/2010 | Chiang et al. |
| 2010/0202043 A1 | 8/2010 | Ujike |
| 2010/0301231 A1 | 12/2010 | Yamaguchi |
| 2010/0323350 A1 | 12/2010 | Gordon et al. |
| 2011/0312841 A1 | 12/2011 | Silverbrook et al. |
| 2013/0035871 A1* | 2/2013 | Mayou ............... A61B 5/14532 702/26 |
| 2014/0087482 A1* | 3/2014 | Nishikawa ......... G01N 21/6452 436/501 |

FOREIGN PATENT DOCUMENTS

| | | |
|---|---|---|
| EP | 2216338 A1 | 8/2010 |
| EP | 2522988 A1 | 11/2012 |
| EP | 2543989 A1 | 1/2013 |
| EP | 2543990 A1 | 1/2013 |
| EP | 2584343 A1 | 4/2013 |
| EP | 2818850 A1 | 12/2014 |
| JP | 04-501956 A | 4/1992 |
| JP | 04-337446 A | 11/1992 |
| JP | 06-113896 A | 4/1994 |
| JP | 2000-106876 A | 4/2000 |
| JP | 2002-507762 A | 3/2002 |
| JP | 2002-543414 A | 12/2002 |
| JP | 2004-506192 A | 2/2004 |
| JP | 2004-121231 A | 4/2004 |
| JP | 2004-187607 A | 7/2004 |
| JP | 2005-98876 A | 4/2005 |
| JP | 2005-099662 A | 4/2005 |
| JP | 2005-308412 A | 11/2005 |
| JP | 2006-333739 A | 12/2006 |
| JP | 2007-020565 A | 2/2007 |
| JP | 2007-20565 A | 2/2007 |
| JP | 4023523 B2 | 12/2007 |
| JP | 2008-58285 A | 3/2008 |
| JP | 2008-116440 A | 5/2008 |
| JP | 2008-536093 A | 9/2008 |
| JP | 2008-292371 A | 12/2008 |
| JP | 2008-298743 A | 12/2008 |
| JP | 2009-145242 A | 7/2009 |
| JP | 2009-250721 A | 10/2009 |
| JP | 2009-281831 A | 12/2009 |
| JP | 2009-288161 A | 12/2009 |
| JP | 2010-019553 A | 1/2010 |
| JP | 2010-190730 A | 9/2010 |
| JP | 2011-2415 A | 1/2011 |
| JP | 2011-033613 A | 2/2011 |
| JP | 2011-036150 A | 2/2011 |
| JP | 2011-508219 A | 3/2011 |
| WO | 88/02785 A2 | 4/1988 |
| WO | 90/06042 A2 | 6/1990 |
| WO | 92/22671 A1 | 12/1992 |
| WO | 98/16814 A1 | 4/1998 |
| WO | 99/47963 A | 9/1999 |
| WO | 00/52451 A1 | 9/2000 |
| WO | 00/66985 A1 | 11/2000 |
| WO | 00/71991 A1 | 11/2000 |
| WO | 02/12864 A1 | 2/2002 |
| WO | 2004/020675 A2 | 3/2004 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/066447 A1 | 5/2009 |
| WO | 2009/117033 A2 | 9/2009 |
| WO | 2010/056579 A1 | 5/2010 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/144528 A1 | 10/2012 |

OTHER PUBLICATIONS

Advisory Action dated Feb. 2, 2016, issued in U.S. Appl. No. 13/746,968.
Official Notice dated Nov. 30, 2015, issued in European application No. 11812369.4.
Prasad V et al. "Topical Review; Confocal microscopy of colloids", Journal of Physics: Condensed Matter, Institute of Physics Publishing, Bristol, GB, vol. 19, No. 11, Mar. 21, 2007, p. 113102.
Non-Final Office Action dated Sep. 28, 2015, issued in U.S. Appl. No. 14/322,010. (10 pages).
Final Office Action dated Sep. 28, 2015, issued in U.S. Appl. No. 13/746,968 (24 pages).
Final Office Action dated Aug. 20, 2015, issued in U.S. Appl. No. 14/172,295 (22 pages).
European Communication Pursuant to Article 94(3) EPC dated Nov. 20, 2014, issued in related European Patent Application No. 11812369.4 (6 pages).
Shuming N. et al., "Real-Time Detection of Single Molecules in Solution by Confocal Fluorescence Microscopy", Analytical Chemistry, American Chemical Society, vol. 67, No. 17, pp. 2849-2857, (1995), Cited in European Communication dated Nov. 20, 2014.
Notice of Reasons for Rejection dated May 19, 2015, issued in corresponding Japanese Patent Application No. 2012-526460 with English translation (8 pages).
Hebert et al., "Spatiotemporal Image Correlation Spectroscopy (STICS) Theory, Verification, and Application to Protein Velocity Mapping in Living CHO Cells", Biophysical Journal, May 2005, vol. 88, No. 5, pp. 3601-3614, cited in Extended European Search Report dated Mar. 26, 2015 (14 pages).
Extended European Search Report dated Mar. 26, 2015, issued in corresponding EP Patent Application No. 12821897.1 (13 pages).
International Search Report dated Aug. 7, 2012, issued in corresponding application No. PCT/JP2012/066576.
Kinjo, M., "Proteins, Nucleic Acids, and Enzymes", vol. 44, No. 9, pp. 1431-1438, 1999; with English translation.
Meyer-Almes, F. J., "Fluorescence Correlation Spectroscopy", R. Rigler, ed., Springer, Berlin, pp. 204-224, 2001.
Kato, N., et al., Genetic Medicine, 2002, vol. 6, No. 2, pp. 271-277; with partial translation.
Kask, P. et al., "Proceedings of the National Academy of Sciences of the United States of America", 1999, vol. 96, pp. 13756-13761.
Sando, S., Kool, E., "Quencher as Leaving Group: Efficient Detection of DNA-Joining Reactions", Journal of the American Chemical Society, vol. 124, No. 10, 2002, pp. 2096.
U.S. Office Action dated Apr. 13, 2015, issued in U.S. Appl. No. 13/746,968 (19 pages).
Extended European Search Report dated Oct. 20, 2014, issued in related EP Application No. 12770835.2 (10 pages).
Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.

(56) References Cited

OTHER PUBLICATIONS

U.S. Office Action dated Apr. 2, 2013, issued in related U.S. Appl. No. 13/596,280 (7 pages).
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability Mar. 30, 2012 (PCT/IPEA/409) issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) dated Mar. 30, 2012, issued in related PCT/JP2011/053482.
Sasaki, Shigeki, "Creation of Functional Recognition Molecules for Chemical Modification of Gene Expression", Yakugaku Zasshi, the Pharmaceutical Society of Japan, 2002, vol. 122, No. 12, p. 1081-1093.
Chinese Office Action dated Feb. 7, 2013, issued in related Chinese application No. 201180011644.5; w/ English Translation (19 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry", Nucleic Acids Research, 1993, vol. 21, No. 4, p. 803-806.
Keller, Richard et al., "Single-Molecule Fluorescence Analysis in Solution", Applied Spectroscopy, 1996, vol. 50, No. 7, p. 12A-32A.
Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.
Li, Haitao et al., "Ultrasensitive Coincidence Fluorescence Detection of Single DNA Molecules", Analytical Chemistry, Apr. 1, 2003, vol. 75, No. 7, p. 1664-1670.
Nie, Shuming et al., "Probing Individual Molecules with Confocal Fluorescence Microscopy", Science, Nov. 11, 1994, vol. 266, p. 1018-1021.
Tahari, Abdel. "Fluorescence Correlation Spectroscopy: Ultrasensitive Detection in Clear and Turbid Media", University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830; with English summary.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243 (7 pages).
Japanese Office Action dated Dec. 18, 2012, issued in related JP application No. 2012-503060; w/ English Translation (6 pages).
Yoshimura, Yoshinaga et al., "Development of Template-Directed Reversible DNA Photocrosslinking", Nucleic Acids Symposium Series, 2008, vol. 10, No. 52, p. 423-424.
Yoshimura, Yoshinaga et al., "Ultrafast Reversible Photo-Cross-Linking Reaction: Toward in Situ DNA Manipulation", Organic Letters, 2008, vol. 10, No. 15, p. 3227-3230.
Takasugi, M. et al., "Sequence-Specific Photo-Induced Cross-Linking of the Two Strands of Double-Helical DNA by a Psoralen Covalently Linked to a Triple Helix-Forming Oligonucleotide", Proc. Natl. Acad. Sci. USA, Jul. 1991, vol. 88, p. 5602-5606.
International Search Report dated Sep. 20, 2011, issued in related PCT/JP2011/066576 (6 pages).
U.S. Office Action dated Feb. 20, 2014, issued in related U.S. Appl. No. 13/746,968 (11 pages).
U.S. Notice of Allowance dated Mar. 27, 2013, issued in related U.S. Appl. No. 13/597,825 (8 pages).
U.S. Office Action dated May 22, 2014, issued in related U.S. Appl. No. 13/746,968 (10 pages).
International Search Report dated Apr. 23, 2013, issued in related PCT/JP2013/053080 (4 pages).
International Search Report dated Jul. 24, 2012, issued in related PCT/JP2012/060137 (6 pages).
International Search Report dated Mar. 5, 2013, issued in related PCT/JP2012/081350 (2 pages).
Chinese Office Action dated Jul. 14, 2014, issued in related Chinese application No. 201180036710.4; w/ English Translation (12 pages).
U.S. Notice of Allowance dated Jun. 19, 2013, issued in co-pending U.S. Appl. No. 13/596,280.
U.S. Notice of Allowance dated Dec. 24, 2013, issued in co-pending U.S. Appl. No. 13/596,243.
Kato, N. et al., "A Single Molecule Analyzer that Enables New Analysis of DNA and Protein Interactions", Gene Medicine, 2002, vol. 6, No. 2, p. 271-277 with English summary.
U.S. Office Action dated Jan. 3, 2013, issued in co-pending U.S. Appl. No. 13/597,825.
Chinese Office Action dated Apr. 20, 2015, issued in Chinese Patent Application No. 201280041270.6 with English translation (11 pages).
Extended European Search Report dated May 20, 2015, issued in European Patent Application No. 12828423.9 (18 pages).
Extended European Search Report dated Feb. 16, 2016 in EP 13764425.8.
U.S. Non-Final Office Action dated Dec. 6, 2016, issued in related co-pending U.S. Appl. No. 14/486,030.
Smoothing, Wikipedia Online entry at http://web.archive.org/web/20110226071633/http://en.wikipedia.org/wiki, Smoothing, Apr. 21, 2017 , p. 1-2.
Office Action dated Feb. 22, 2017, issued in counterpart European Application No. 12828423.9. (6 pages).
Extended European Search Report dated Oct. 2, 2017, issued in related European patent application No. 11750482.9.
Extended European Search Report dated Sep. 29, 2017, issued in related European patent application No. 11750483.7.

* cited by examiner

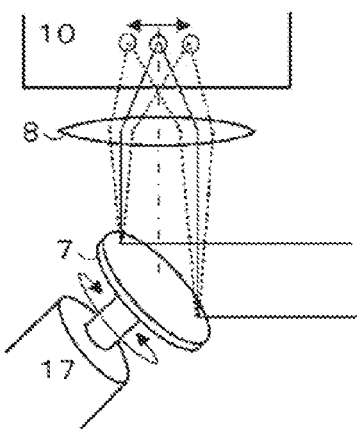
FIG. 1C
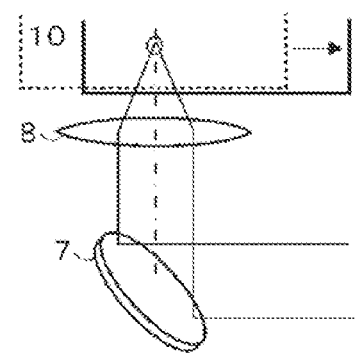
FIG. 1D
FIG. 2A
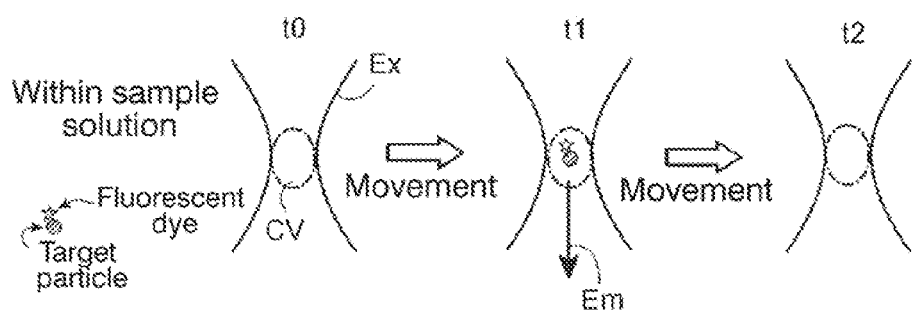
FIG. 2B
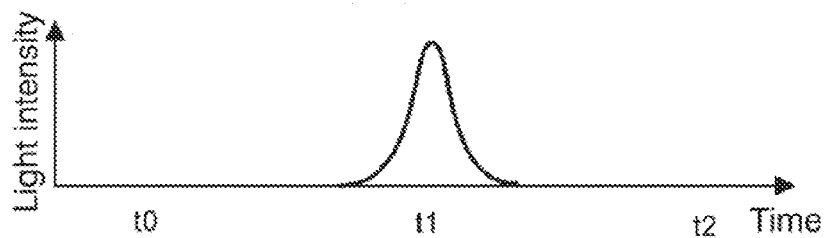

METHOD FOR DETECTING TARGET PARTICLE

BACKGROUND OF THE INVENTION

Field of the Invention

The present invention relates to a method for determining the concentration of particles dispersed and moving randomly in a sample solution and bound to particles for separation and recovery by solid-liquid separation treatment using an optical system capable of detecting light from a microregion in the solution, such as an optical system of a confocal microscope and multi-photon microscope.

The present application claims priority on the basis of Japanese Patent Application No. 2011-187600, filed in Japan on Aug. 30, 2011, the contents of which are incorporated herein by reference. The present application is a U.S. continuation application based on the PCT International Patent Application, PCT/JP2012/066576, filed on Jun. 28, 2012; the contents of which are incorporated herein by reference.

Description of the Related Art

Due to progress made in the field of optical measurement technology in recent years, it has become possible to detect and measure feint light at the level of a single photon or single fluorescent molecule using the optical system of a confocal microscope and ultra-high-sensitivity photodetection technology capable of performing photon counting (detecting individual photons). Therefore, various devices or methods have been proposed that detect interactions between molecules such as biomolecules or coupling and dissociation reactions between molecules using such feint light measurement technology. For example, in fluorescence correlation spectroscopy (FCS: see, for example, Japanese Unexamined Patent Application, First Publication No. 2005-098876; Japanese Unexamined Patent Application, First Publication No. 2008-292371; Japanese Unexamined Patent Application, First Publication No. 2009-281831; Kinjo, M., Proteins, Nucleic Acids and Enzymes, 1999, Vol. 44, No. 9, pp. 1431-1438; Meyer-Almes, Fluorescence Correlation Spectroscopy, R. Rigler, ed., Springer, Berlin, 2000, pp. 204-224; and Katoh, N., et al., Gene and Medicine, 2002, Vol. 6, No. 2, pp. 271-277), fluorescence intensity is measured from fluorescent molecules or fluorescent-labeled molecules (such as fluorescent molecules) entering and leaving a microregion (a region where laser light of a microscope is focused; referred to as confocal volume) in a sample solution using the optical system of a laser confocal microscope and photon counting technology. Information such as the speed of movement or the size or concentration of fluorescent molecules and the like is acquired, or various phenomena in the manner of changes in molecular structure or size, molecule coupling and dissociation reactions or dispersion and aggregation are detected, based on the average retention time (transitional diffusion time) of fluorescent molecules and the like in the microregion and the average value of the number of molecules remaining therein determined from the value of an autocorrelation function of the measured fluorescence intensity. In addition, in fluorescence intensity distribution analysis (FIDA: see, for example, Japanese Patent (Granted) Publication No. 4023523) and photon counting histograms (PCH: see, for example, International Publication No. WO 2008-080417), a histogram is generated of the fluorescence intensity of fluorescent molecules and the like entering and leaving a measured confocal volume in the same manner as FCS. By fitting a statistical model formula to the distribution of that histogram, the average value of the characteristic brightness of the fluorescent molecules and the like and the average value of the number of molecules remaining in the confocal volume are calculated, and changes in molecular structure and size, coupling and/or dissociation, or dispersion or aggregation and the like are then estimated based on this information. Moreover, Japanese Unexamined Patent Application, First Publication No. 2007-20565 and Japanese Unexamined Patent Application, First Publication No. 2008-116440 propose a method for detecting a fluorescent substance based on the time lapse of a fluorescent signal of a sample solution measured using the optical system of a confocal microscope. Japanese Unexamined Patent Application, First Publication No. H04-337446 proposes a signal arithmetic processing technology for detecting the presence of fluorescent fine particles in a flow or on a substrate by measuring feint light from fluorescent fine particles that have passed through a flow cytometer or fluorescent fine particles immobilized on a substrate using photon counting technology.

In particular, according to methods using microregion fluorescence measurement technology using the optical system of a confocal microscope and photon counting technology in the manner of FCS or FIDA and the like, the sample required for measurement is only required to be of an extremely low concentration and extremely small amount in comparison with that used in the past (since the amount used for a single measurement is roughly only several tens of microliters) and measurement time is shortened considerably (measurement of a duration on the order of several seconds for a single measurement is repeated several times). Thus, these technologies are expected to be utilized as powerful tools that make it possible to carry out experimentation or testing less expensively and faster in comparison with conventional biochemical methods in the case of performing analyses on scarce or expensive samples frequently used in fields such as medical or biochemical research and development, or in the case of a large number of specimens such as when clinically diagnosing diseases or screening physiologically active substances.

SUMMARY OF THE INVENTION

As a result of conducting extensive research to solve the aforementioned problems, the inventors of the present invention found that, in the case of indirectly detecting a particle dispersed and randomly moving in a sample solution by using as an indicator thereof light released from a luminescent probe bound to the particle, by detecting the particle bound to the luminescent probe using a scanning molecule counting technology, even in the case the concentration of target particles in the sample solution is extremely low, the particle bound to the luminescent probe can be detected with favorable sensitivity. Moreover, by counting the number of a complex composed of a target particle, luminescent probe and particle for separation and recovery by carrying out measurement according to the scanning molecule counting method on a target particle labeled with a luminescent probe, it was found that the target particle can be detected with high accuracy, thereby leading to completion of the present invention.

Here, the scanning molecule counting method refers to a novel optical analysis technology proposed by the present applicant in Japanese Patent Application No. 2010-044714.

Namely, the present invention provides a method for detecting a target particle as described below.

(1) A method for detecting a target particle dispersed and randomly moving in a solution, comprising:

(a) preparing a solution containing a target particle, a luminescent probe that binds to the target particle and a particle for separation and recovery that is capable to be bound to a complex composed of the target particle and the luminescent probe, or containing the target particle bound to the luminescent probe, the luminescent probe and the particle for separation and recovery, and forming a complex comprising the target particle, the luminescent probe and the particle for separation and recovery in the solution, (b) recovering the particle for separation and recovery from the solution by solid-liquid separation treatment after the (a), and preparing a sample solution containing the particles for separation and recovery, and (c) calculating the number of the complex present in the sample solution prepared in the (b), thereby detecting the target particle;

the particle for separation and recovery binds to a complex composed of the target particle and the luminescent probe in (a), and the calculating of the number of the complex in the (c) being carried out by:

detecting light released from the complex in the photodetection region, while moving the location of the photodetection region of the optical system in the sample solution using the optical system of a confocal microscope or multiphoton microscope, individually detecting the complex from the detected light by individually detecting optical signals from individual complexes dispersed and randomly moving in the solution, and counting the number of target particles detected during movement of the location of the photodetection region by counting the number of individually detected complexes.

(2) The method for detecting a target particle described in (1) above, wherein the sedimentation rate of the particle for separation and recovery in the sample solution is $1 \times 10^{-6}$ m/s or less.

(3) The method for detecting a target particle described in (1) or (2) above, wherein, in the moving of the location of the photodetection region, the location of the photodetection region is moved along a second path over which the location thereof moves along a first path.

(4) The method for detecting a target particle described in (3) above, wherein the first and second paths are circulation paths, and the movement cycle of the location of the photodetection region along the second path is shorter than the movement cycle of the location of the second path along the first path.

(5) The method for detecting a target particle described in (3) or (4) above, wherein a movement cycle $\tau 1$ of the location of the photodetection region, a movement speed $v2$ of the location of the second path, and a diameter $d$ of the photodetection region satisfy the following relational expression:

$$v2 \cdot \tau 1 > d.$$

(6) The method for detecting a target particle described in any of (3) to (5) above, wherein, the location of the photodetection region moves along the second path by changing the light path of the optical system, and the location of the second path in the sample solution moves along the first path by moving the location of the sample solution.

(7) The method for detecting a target particle described in any of (3) to (6) above, wherein the second path is circular or elliptical, and the first path is circular, elliptical or linear.

(8) The method for detecting a target particle described in any of (1) to (7), wherein, in the moving of the location of the photodetection region, the location of the photodetection region moves at a speed faster than the diffusion movement speed of the complex.

(9) The method for detecting a target particle described in any of (1) to (8) above, wherein, in the individually detecting of the complex by individually detecting optical signals from individual complexes from the detected light, the entry of a single complex into the photodetection region is detected based on the form of a chronologically detected light signal.

(10) The method for detecting a target particle described in any of (1) to (9) above, wherein the particle for separation and recovery is a magnetic particle.

BRIEF DESCRIPTION OF THE DRAWINGS

FIG. 1C is a schematic diagram of a mechanism for moving the location of a photodetection region in a sample solution by changing the orientation of a mirror 7.

FIG. 1D is a schematic diagram of a mechanism for moving the location of a sample solution by moving the location of a microplate in the horizontal direction.

FIG. 2A is a schematic diagram explaining the principle of photodetection using optical analysis technology for a scanning molecule counting method.

FIG. 2B is a schematic diagram of time-chronological changes in light intensity measured with a scanning molecule counting method.

DETAILED DESCRIPTION OF THE PREFERRED EMBODIMENTS

Figure 1A:
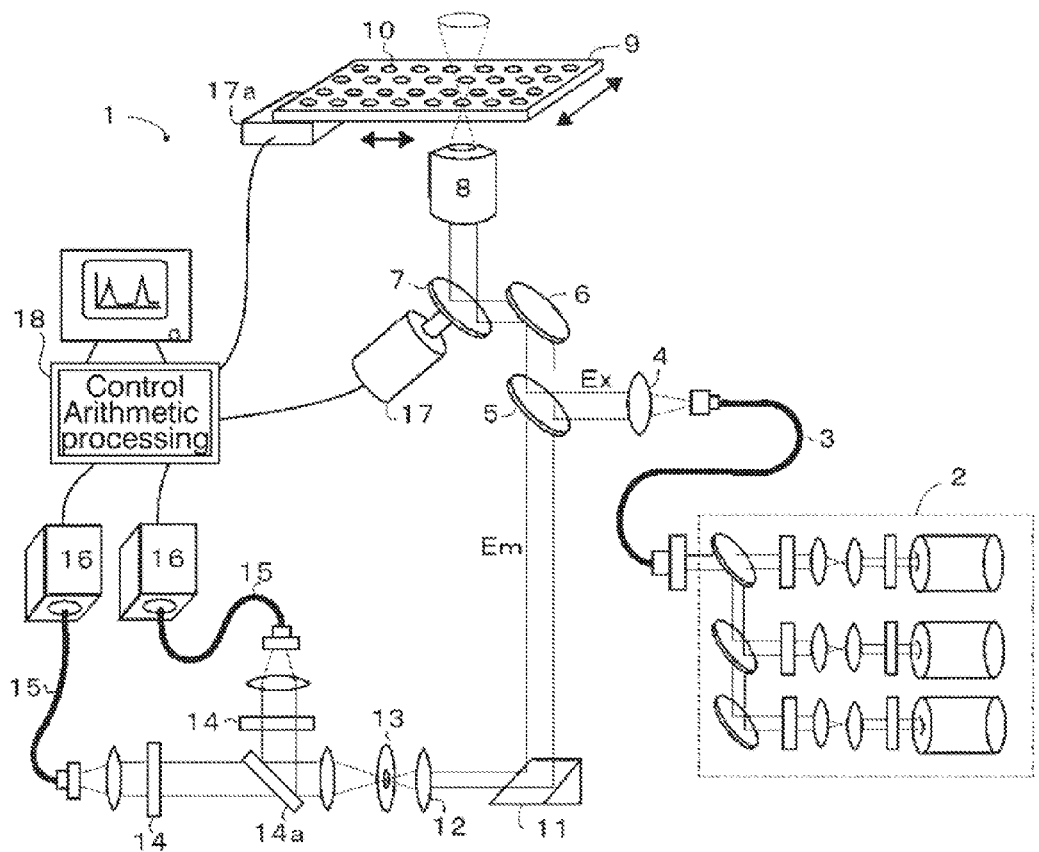
FIG. 1A is a schematic diagram of the internal structure of an optical analysis device for a scanning molecule counting method.

The following provides an explanation of an embodiment relating to the method for detecting a target particle of the present invention.

An explanation is first provided of the scanning molecule counting method. The scanning molecule counting method is a technique for counting luminescent particles, or acquiring information relating to concentration or number density of luminescent particles in a sample solution, by detecting light emitted from the luminescent particles in a microregion and individually detecting each of the luminescent particles in a sample solution when the particles emitting light that disperse and move randomly in a sample solution (referring to the aforementioned "luminescent particles") cross a microregion while scanning the sample solution by microregions. In the scanning molecule counting method, only an extremely small amount (for example, in the order of only several tens of microliters) of sample is required for measurement in the same manner as optical analysis technologies such as FIDA, measurement time is short, and properties such as concentration or number density can be quantitatively detected for luminescent particles at a lower concentration or number density than in the case of optical analysis technologies such as FIDA.

Furthermore, luminescent particles refer to particles that emit light by fluorescence, phosphorescence, chemiluminescence, bioluminescence or light scattering and the like. In the method used to quantify target particles of the present invention, particles in which target particles and luminescent probe are bound are luminescent particles.

In the present embodiment and description of the present application, a "photodetection region" of the optical system of a confocal microscope or multi-photon microscope refers to a microregion in which light is detected by the microscope, and in the case illumination light is imparted from an object lens, corresponds to the region where that illumination light is focused. This region is defined by the positional relationship between the object lens and pinhole in a confocal microscope in particular. In the case luminescent particles emit light in the absence of illumination light, such as in the case of particles that emit light by chemiluminescence or bioluminescence, the microscope does not require illumination light. Furthermore, in the present description, a "signal" of a luminescent particle refers to a signal representing light from a luminescent particle unless specifically indicated otherwise.

Light is successively detected while moving the location of the photodetection region in a sample solution, or in other words, while scanning the sample solution by photodetection regions. Whereupon, when the photodetection region being moved contains a luminescent probe bound to or associated with a randomly moving particle, light from the luminescent probe is detected, and as a result, the presence of a single particle is detected (although depending on the mode of the experiment, the luminescent probe may also dissociate from the particle desired to be detected (target particle) during detection of light after having bound to that particle desired to be detected). Optical signals from the luminescent probe are individually detected in the successively detected light, and as a result thereof, the presence of individual particles (particles bound to the luminescent probe) is successively detected and various information relating to the state of the particles in the solution is acquired. More specifically, in the aforementioned configuration, for example, the number of particles detected during movement of the location of the photodetection region may be counted by counting individually detected particles (particle counting). According to this configuration, information relating to number density or concentration of particles in a sample solution is obtained by combining the number of particles and the amount of movement of the location of the photodetection region. In particular, particle number density or concentration can be specifically calculated by, for example, moving the location of the photodetection region at a prescribed speed by an arbitrary method, and specifying the total volume of the movement locus of the location of the photodetection region. Naturally, instead of determining absolute values for number density or concentration directly, relative number density or concentration may also be determined relative to a plurality of sample solutions or reference sample solution having a standard concentration or number density.

In addition, in the scanning molecule counting method, a configuration may be employed that allows the location of the photodetection region to be moved by changing the light path of the optical system. According to this configuration, movement of the photodetection region is rapid, and mechanical vibrations or actions attributable to fluid dynamics do not substantially occur in the sample solution. Thus, light can be measured with the particles targeted for detection in a stable state without being affected by dynamic action (if vibrations or flow act in the sample solution, the physical properties of the particles may change). Since it is also not necessary to provide a configuration that allows a sample solution to flow there through in the scanning molecule counting method, measurements and analyses can be carried out on an extremely small amount of sample solution (on the order of one to several tens of microliters) in the same manner as in the case of FCS or FIDA and the like.

In the aforementioned individually detecting of particles, a judgment as to whether or not a luminescent probe bound to a single particle (including the state in which a single luminescent probe is bound to a single particle, the case in which a plurality of luminescent probes are bound to a single particle, and the case in which a luminescent probe has dissociated from a particle after having bound to a single particle depending on the mode of the experiment) has entered the photodetection region based on chronologically detected light signals may be carried out based on the form of a chronologically detected light signal. In this embodiment, the entry of a luminescent probe bound to a single particle into the photodetection region is typically detected when a light signal has been detected that has intensity greater than a prescribed threshold value. More specifically, a signal representing light from a luminescent particle normally appears as a chronologically detection value of a photodetector, or in other words, a bell-shaped pulsed signal having intensity of a certain degree or higher in light intensity data. Noise is not in the form of a bell-shaped pulsed signal or appears as a signal of low intensity. Therefore, a pulsed signal having intensity greater than a prescribed threshold value may be detected as a signal representing light from a single luminescent particle in time series light intensity data. The "threshold value" can be experimentally set to a suitable value.

In addition, in the aforementioned moving of the location of the photodetection region, the movement speed of the location of the photodetection region in a sample solution may be suitably changed based on the properties of the luminescent probe bound to a particle or the number density or concentration thereof in a sample solution. As is understood by persons skilled in the art, the mode of light detected from a luminescent probe bound to a particle can be changed according to the properties thereof or the number density or concentration in a sample solution. In particular, since the amount of light obtained from a luminescent probe bound to a single particle decreases as the movement speed of the photodetection region increases, the movement speed of the photodetection region may be suitably changed so that light from the luminescent probe bound to a single particle can be measured with favorable accuracy and sensitivity.

Moreover, in the aforementioned moving of the location of the photodetection region, the movement speed of the location of the photodetection region in a sample solution may be set to be faster than the diffusion movement speed (average speed of particles moving by Brownian movement) of the luminescent probe bound to a particle to be detected (luminescent probe bound to a target particle in the method used to quantify target particles of the present embodiment). As was previously explained, in the scanning molecule counting method, light emitted from a luminescent probe bound to a single particle is detected when a photodetection region has passed through a location where that luminescent probe is present, thereby resulting in individual detection of the luminescent probe. However, in the case the luminescent probe bound to a particle moves randomly through a solution by Brownian movement and enters and leaves the photodetection region a plurality of times, optical signals (optical signals indicating the presence of a particle desired to be detected) from a single luminescent probe end up being detected a plurality of times, and it becomes difficult to make a detected light signal correspond to the presence of a single particle desired to be detected. Therefore, as was previously described, the movement speed of the photodetection region is set to be faster than the diffusion movement speed of the luminescent probe bound to a particle (and more specifically, the movement speed of the photodetection region is set so as to move at a speed faster than the diffusion movement speed of a luminescent probe in a state of being bound to a target particle), and as a result, a luminescent probe bound to a single particle can be made to correspond to a single light signal (light signal representing the presence of a particle). Furthermore, since diffusion movement speed varies according to the luminescent probe bound to a particle, the movement of the photodetection region may be suitably changed corresponding to the properties (and particularly, the diffusion constant) of the luminescent probe bound to a particle as previously described.

Changing of the light path of the optical system used to move the location of the photodetection region may be carried out by an arbitrary method.

For example, the location of the photodetection region may be changed by changing the light path using a galvanometer mirror employed in laser scanning optical microscopes. The movement locus of the location of the photodetection region may be set arbitrarily, and the movement locus of the location of the photodetection region may be selected from among, for example, a circular, oval, rectangular, linear or curved locus.

In the scanning molecule counting method, since the photodetection mechanism per se is composed so as to detect light from a photodetection region of a confocal microscope or multi-photon microscope in the same manner as in the case of optical analysis technologies such as FIDA, the amount of sample solution may also similarly be an extremely small amount. However, in the scanning molecule counting method, since statistical processing involving calculation of fluctuations in fluorescent intensity and the like is not carried out, optical analysis technology employing the scanning molecule counting method can be applied to sample solutions in which the number density or concentration of particles is considerably lower than the level required by conventional optical analysis technologies such as FIDA.

In addition, in the scanning molecule counting method, since each particle dispersed or dissolved in a solution is detected individually, counting of particles, determination of particle concentration or number density in a sample solution, or acquisition of information relating to concentration or number density, can be carried out quantitatively using that information. Namely, according to the scanning molecule counting method, since particles are detected one at a time by creating a 1:1 correlation between a particle passing through a photodetection region and a detected light signal, particles dispersed and moving randomly in a solution can be counted, and the concentration or number density of particles in a sample solution can be determined more accurately than in the prior art. In actuality, according to the method used to quantify a target particle of the present embodiment comprising individually detecting a luminescent probe bound to a target particle and then counting the number thereof to determine particle concentration, the target particles can be measured quantitatively even if the concentration of a luminescent probe bound to target particles in a sample solution is lower than the concentration able to be determined based on fluorescence intensity as measured with a fluorescence spectrophotometer or plate reader.

Moreover, according to a mode in which a sample solution is scanned by photodetection regions by changing the light path of the optical system, the sample solution is observed uniformly or the sample solution is observed in a mechanically stable state without imparting mechanical vibrations or actions attributable to fluid dynamics to the sample solution. Thus, the reliability of quantitative detection results is improved in comparison with the case of causing the generation of flow in a sample (in the case of imparting flow to a sample, in addition to it being difficult to impart a uniform flow at all times, the configuration of the device becomes complex, and together with causing a considerable increase in the amount of sample required, the particles in solution, luminescent probe, complex thereof or other substances may undergo deterioration or degeneration due to the fluid dynamic action generated by that flow), and measurements can be carried out in a state that does not impart effects caused by dynamic action or artifacts to particles to be detected in a sample solution.

<Configuration of Optical Analysis Device for Scanning Molecule Counting Method>

Figure 1B:
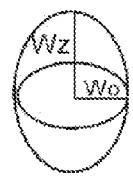
FIG. 1B is a schematic diagram of a confocal volume (observation region of a confocal microscope).

As schematically exemplified in FIG. 1A, the scanning molecule counting method can be realized by an optical analysis device having a basic configuration composed by combining the optical system of a confocal microscope capable of performing FCS or FIDA and the like with a photodetector. As shown in the same drawing, an optical analysis device 1 is composed of optical system components 2 to 17, and a computer 18 for controlling the operation of each component of the optical system components and acquiring and analyzing data. The optical system of the optical analysis device 1 may be composed in the same manner as the optical system of an ordinary confocal microscope, laser light (Ex) that has propagated from a light source 2 through a single-mode optic fiber 3 is radiated therein in the form of light that diverges at an angle determined according to a characteristic NA at the outgoing end of the fiber, and the laser light is converted to parallel light by a collimator 4 and is reflected by a dichroic mirror 5 and reflecting mirrors 6 and 7, after which it enters an object lens 8. A microplate 9, in which are arranged sample containers or wells 10 into which are dispensed one to several tens of microliters of a sample solution, is typically arranged above the object lens 8, and laser light emitted from the object lens 8 is focused on the sample solution in the sample containers or wells 10, forming a region of high light intensity (excitation region). A target particle, a luminescent probe that binds to the particle, and typically a molecule having a luminescent label such as a fluorescent dye added thereto, are dispersed or dissolved in the sample solution, and when a particle bound to or associated with the luminescent probe (or the luminescent probe may dissociate from the particle after having initially bound thereto depending on the mode of the experiment) enters the excitation region, the luminescent probe is excited and light is released during that time. The released light (Em) passes through the object lens 8 and dichroic mirror 5, is reflected by a mirror 11, is concentrated by a condenser lens 12 and then passes through a pinhole 13 followed by passing through a barrier filter 14 (here, only light components of a specific wavelength band are selected), after which the released light is introduced into a multi-mode optic fiber 15 and reaches a photodetector 16, and after being converted to a chronological electrical signal, is input to the computer 18 where processing for optical analysis is carried out by a mode to be subsequently explained. Furthermore, as is understood by persons skilled in the art, in the aforementioned configuration, the pinhole 13 is arranged at a location conjugate to the focal position of the object lens 8, and as a result thereof, only light emitted from the focused region of the laser light as schematically shown in FIG. 1B, namely light emitted from the excitation region, passes through the pinhole 13, while light from a location other than the excitation region is blocked. The focused region of the laser light exemplified in FIG. 1B is normally a photodetection region in the present optical analysis device having an effective volume of about 1 fL to 10 fL, and is referred to as the confocal volume (and typically has a Gaussian distribution or Lorentzian distribution in which light intensity reaches a peak in the center of the region, and effective volume is the volume of a roughly ellipsoidal shape in which the boundary of light intensity is plane defined as 1/e2). In addition, in the scanning molecule method, since light is detected from a complex consisting of a single particle and luminescent probe or light from a luminescent probe, and for example, feint light is detected from one or a plurality of fluorescent dye molecules, an ultra-high-sensitivity photodetector capable of use in photon counting may be used for the photodetector 16. In addition, the stage of the microscope (not shown) may be provided with a stage position adjustment device 17a for moving the location of the microplate 9 in the horizontal direction in order to change the well 10 to be observed. Operation of the stage position adjustment device 17a may be controlled by the computer 18. As a result of employing this configuration, measurements can be carried out rapidly even in the case of multiple specimens.

Moreover, in the optical system of the aforementioned optical analysis device, a mechanism is provided for scanning the sample solution by photodetection regions by changing the light path of the optical system, namely a mechanism for moving the location of the focused region (photodetection region) in the sample solution. A mirror light deflector 17 that changes the orientation of the reflecting mirror 7, for example, may be employed as a mechanism for moving the location of the photodetection region in this manner as schematically exemplified in FIG. 1C. This mirror light deflector 17 may be composed in the same manner as a galvanometer mirror device provided in ordinary laser scanning optical microscopes (system in which the location of the photodetection region is moved). In addition, the stage position adjustment device 17a may be operated so as to move the relative location of the photodetection region in the sample solution by moving the location of the container 10 (microplate 9) injected with sample solution in the horizontal direction (system in which the location of the sample solution is moved). Simultaneous to causing the photodetection region to circle along a scanning track (second path) by a system that moves the relative location of the photodetection region by changing the light path as previously described, the location of the scanning track of the photodetection region in the sample solution is moved along a prescribed movement path (first path) by a system that moves the location of the sample solution. In the case of either system, the mirror light deflector 17 is driven in coordination with light detection by the photodetector 16 under the control of the computer 18 so as to achieve a desired movement pattern of the location of the photodetection region. The movement locus of the location of the photodetection region is arbitrarily selected from among a circular, oval, rectangular, linear and curved locus or a combination thereof (or various movement patterns programmed in the computer 18 can be selected). Furthermore, although not shown in the drawings, the location of the photodetection region may be moved in the vertical direction by moving the object lens 8 up and down. As was previously described, according to a configuration that moves the location of the photodetection region by changing the light path of the optical system instead of a configuration that moves a sample solution, there is no substantial occurrence of mechanical vibrations or actions attributable to fluid dynamics in the sample solution, and the effects of dynamic action on a target can be eliminated, thereby making it possible to achieve stable measurements.

In the case a conjugate of a particle and luminescent probe or a luminescent probe emits light as a result of multi-photon absorption, the aforementioned optical system is used in the form of a multi-photon microscope. In that case, since light is only released in the focused region of the excitation light (photodetection region), the pinhole 13 may be omitted. In addition, in the case a conjugate of a particle and luminescent probe or a luminescent probe emits light by chemiluminescence or bioluminescent phenomena without depending on excitation light, optical system components 2 to 5 for generating excitation light may be omitted. In the case a conjugate of a particle and luminescent probe or a luminescent probe emits light by phosphorescence or light scattering, the aforementioned optical system of a confocal microscope is used as is. Moreover, in the optical analysis device 1, a plurality of excitation light sources 2 are provided as shown in the drawings, and these may be composed so as to allow the wavelength of the excitation to be suitably selected according to the wavelength of light that excites a conjugate of a particle and luminescent probe or a luminescent probe. Similarly, a dichroic mirror 14a may be inserted into the light path of the detection light, and light may be detected separately by a plurality of photodetectors 16 by dividing the detected light into a plurality of wavelength bands. According to this configuration, in the case of detecting information relating to emission wavelength properties (emission spectrum) of luminescent particles or in the case a plurality of types of luminescent particles are contained, the light therefrom can be separately detected according to the wavelength thereof. Moreover, with respect to light detection, light that has been polarized in a prescribed direction may be used as excitation light, and the polarization properties of luminescent particles may be allowed to be detected by individually detecting those components of the detected light in a direction perpendicular to the polarization direction of the excitation light. In that case, a polarizer (not shown) is inserted into the light path of the excitation light, and a polarizing beam splitter 14a is inserted into the light path of the detection light.

<Principle of Optical Analysis Technology of Scanning Molecule Counting Method>

In comparison with conventional biochemical analysis technologies, spectral analysis technologies such as FIDA are superior in that they require only an extremely small amount of sample and allow testing to be carried out rapidly. However, in the case of spectral analysis technologies such as FIDA, the concentration and properties of target particles are in principle determined based on fluctuations in fluorescence intensity. Thus, in order to obtain measurement results of favorable accuracy, the concentration or number density of target particles in a sample solution is required to be of a level such that roughly one observation target particle is present at all times in a photodetection region CV during measurement of fluorescence intensity, and that significant light intensity (photon count) be detected at all times during the measurement time. If the concentration or number density of the target particles is lower than that level, such as in the case of being at a level such that target particles only occasionally enter the photodetection region CV, significant light intensity (photon count) only appears during a portion of the measurement time, thereby making it difficult to accurately determine fluctuations in light intensity. In addition, in the case the concentration of target particles is considerably lower than the level at which roughly one target particle is present in the photodetection region at all times during measurement, determination of fluctuations in light intensity is subject to background effects, thereby prolonging measurement time in order to obtain an adequate amount of meaningful light intensity data for making a determination. In contrast, in the scanning molecule counting method, the concentration, number density or other properties of target particles can be detected even in the case the concentration of target particles is lower than the level required by spectral analysis technologies such as FIDA.

In the processing carried out using the optical analysis technology of the scanning molecule counting method, in plain terms, photodetection is carried out by changing the light path by driving a mechanism (mirror light defector 17) while moving the location of the photodetection region CV in a sample solution, or in other words, while scanning the interior of a sample solution with the photodetection region CV, as is schematically depicted in FIGS. 2A to 2E.

This being the case, as shown in FIG. 2A, for example, when it passes a region in which a single particle (a luminescent probe in the form of a fluorescent dye is bound to the particle in FIG. 2A) is present (t1) during the time the photodetection region CV moves (time t0 to t2 in the drawing), significant light intensity (Em) is detected as depicted in FIG. 2B. Thus, movement of the location of the photodetection region CV and photodetection are carried out as described above, particles bound to a luminescent probe are individually detected as a result of significant light intensity being detected for each particle that appears during that time as exemplified in FIG. 2B, and by counting the number of those particles, the number of particles present in a measured region, or information relating to concentration or number density thereof, can be acquired. In this principle of the optical analysis technology of the scanning molecule counting method, since individual particles are detected without carrying out statistical arithmetic processing so as to determine fluctuations in fluorescence intensity, it should be understood that information relating to particle concentration or number density can be acquired even in a sample solution in which the concentration of particles to be observed is so low that they cannot be analyzed by FIDA and the like with adequate accuracy.

In addition, according to a method by which particles in a sample solution are individually detected and counted as in the scanning molecule counting method, measurements can be carried out at a lower concentration than in the case of measuring the concentration of fluorescent-labeled particles based on fluorescence intensity measured with a fluorescence spectrophotometer or plate reader. In the case of measuring the concentration of fluorescent-labeled particles with a fluorescence spectrophotometer or plate reader, fluorescence intensity is normally assumed to be proportional to the concentration of the fluorescent-labeled particles. In this case, however, if the concentration of the fluorescent-labeled particles becomes low enough, the amount of noise increases relative to the size of the signal generated from light emitted from the fluorescent-labeled particles (resulting in a poor S/N ratio). As a result, the proportional relationship between the concentration of fluorescent-labeled particles and light signal strength is disrupted, and the accuracy of determined concentration values becomes poor. On the other hand, in the scanning molecule counting method, since noise signals are removed from detection results in the detecting of signals corresponding to individual particles among detected light signals, particles can be detected at a lower concentration than that in the case of detecting concentration based on the assumption of fluorescence intensity being proportional to the concentration of fluorescent-labeled particles.

Moreover, in the case a plurality of luminescent probes are bound to a single target particle, according to a method for individually detecting and counting particles in a sample solution in the manner of the scanning molecule counting method, particle concentration measurement accuracy can be improved for high particle concentrations to a greater degree than conventional methods consisting of determining concentration based on the assumption of fluorescence intensity being proportional to the concentration of fluorescent-labeled particles. In the case a plurality of luminescent probes are bound to a single target particle, when a certain amount of luminescent probe is added to the sample solution, the number of luminescent probes that bind to the particles undergoes a relative decrease as the concentration of target particles increases. In this case, since fluorescence intensity per single target particle decreases, the proportional relationship between the concentration of fluorescent-labeled particles and the amount of light is disrupted, and accuracy of determined concentration values becomes poor. On the other hand, in the scanning molecule counting method, since, in the detecting of signals corresponding to individual particles among detected light signals, concentration is determined based on the number of particles with little effect of reductions in fluorescence intensity per particle, particles can be detected at higher concentrations than in the case of detecting concentration based on the assumption that fluorescence intensity is proportional to the concentration of fluorescent-labeled particles.

<Measurement of Light Intensity of Sample Solution by Scanning Molecule Counting Method>

Measurement of light intensity in optical analyses using the scanning molecule counting method may also be carried out by a mode similar to the fluorescence intensity measurement in FCS or FIDA with the exception of moving the location of a photodetection region in a sample solution (scanning the interior of the sample solution) by driving the mirror light deflector 17 during measurement. During operational processing, sample solution is typically injected into the wells 10 of the microplate 9, and after placing the microplate 9 on the microscope stage, when a user inputs instructions for starting measurement to the computer 18, the computer 18 initiates radiation of excitation light and measurement of light intensity in a photodetection region in the sample solution in accordance with a program (consisting of a procedure for changing the light path so as to move the location of the photodetection region in the sample solution and a procedure for detecting light from the photodetection region during movement of the location of the photodetection region) stored in a memory device (not shown). During the time this measurement is being carried out, the mirror light deflector 17 drives the mirror 7 (galvanometer mirror) under the control of a processing operation in accordance with the program of the computer 18, the location of the photodetection region is moved in the wells 10, and at the same time, the photodetector 16 converts successively detected light to electrical signals and transmits those signals to the computer 18, where the computer 18 generates and stores chronological light intensity data from the transmitted light signals. Furthermore, since the photodetector 16 is typically an ultra-high-sensitivity photodetector capable of detecting the arrival of a single photon, light detection is in the form of photon counting that is carried out in a mode in which the number of photons arriving at the photodetector in a prescribed unit time period (bin time), such as every 10 µs, is successively measured over a prescribed amount of time, and the chronological light intensity data is in the form of chronological photon count data.

The movement speed when moving the location of the photodetection region during measurement of light intensity may be an arbitrary speed, and for example, may be a prescribed speed set experimentally or so as to comply with the analysis objective. In the case of acquiring information relating to particle number density or concentration based on the number of target particles detected, since the region through which the photodetection region passes is required to have a certain size or volume, the location of the photodetection region is moved by a mode that allows movement distance to be determined. Furthermore, since the presence of a proportional relationship between elapsed time during measurement and movement distance of the location of the photodetection region facilitates interpretation of measurement results, movement speed may be basically made to be a constant speed, although not limited thereto.

Figure 3A:
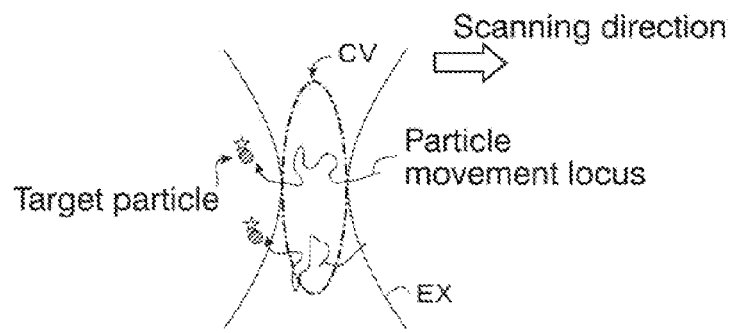
FIG. 3A is a model diagram of the case of a target particle crossing a photodetection region while demonstrating Brownian movement.
Figure 3B:
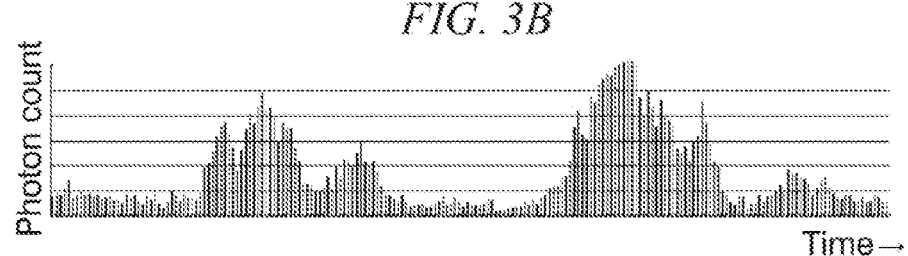
FIG. 3B is a drawing showing an example of chronological changes in a photon count (light intensity) in the model diagram of FIG. 3A.
Figure 4A:
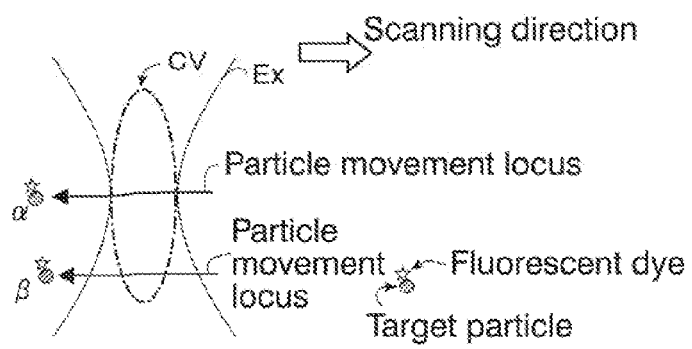
FIG. 4A is a model diagram of the case of a target particle crossing a photodetection region by moving the location of the photodetection region in a sample solution at a speed faster than the diffusion movement speed of the target particles.
Figure 4B:
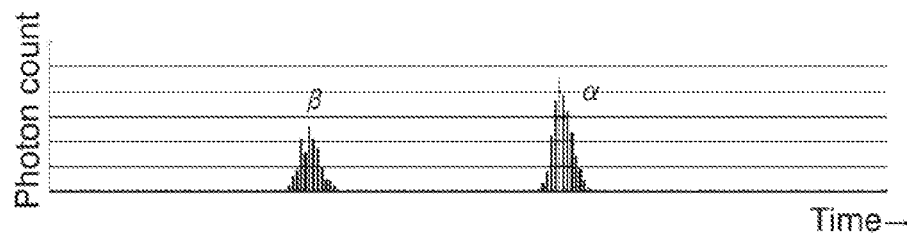
FIG. 4B is a drawing showing an example of chronological changes in photon count (light intensity) in the model diagram of FIG. 4A.

However, with respect to movement speed of the location of the photodetection region, in order to quantitatively detect individual target particles or count the number of target particles based on chronologically measured light intensity data with favorable accuracy, the movement speed may be set to value that is faster than the random movement speed of the target particles (and more precisely, conjugates of particles and luminescent probe or luminescent probe that has degraded and been released after binding with the particles, and in the present embodiment, target particles bound to a luminescent probe), or in other words, a speed faster than movement speed attributable to Brownian movement. Since target particles in an optical analysis technology using the scanning molecule counting method are particles that are dispersed or dissolved in a solution and randomly move about freely therein, their locations based on Brownian movement move over time. Thus, in the case movement speed of the location of the photodetection region is slower than movement attributable to Brownian movement, particles randomly move through the region as schematically depicted in FIG. 3A, and as a result thereof, light intensity changes randomly as depicted in FIG. 3B (and as was previously mentioned, excitation light intensity in a photodetection region has its peak in the center of the region and then decreases moving to either side), thereby making it difficult to specify significant changes in light intensity corresponding to individual target particles. Therefore, the movement speed of the location of the photodetection region may be set to be faster than the average movement speed attributable to Brownian movement (diffusion movement speed) so that particles cross the photodetection region in nearly a straight line as depicted in FIG. 4A, and as a result thereof, a profile of the change in light intensity corresponding to individual particles becomes nearly uniform as exemplified in FIG. 4B in the chronological light intensity data (in the case particles cross the photodetection region in nearly a straight line, the profile of changes in light intensity is roughly the same as the distribution of excitation light intensity), and the correspondence between individual target particles and light intensity can be easily determined.

More specifically, a time $\Delta t$ required for a target particle having a diffusion coefficient D (and more precisely, a conjugate of a particle and luminescent probe or a luminescent probe that has been degraded and released after binding with the particle) to pass through a photodetection region (confocal volume) having a diameter Wo by Brownian movement can be determined from the following relational expression of mean square displacement:

$$(2Wo)^2 = 6D \cdot \Delta t \quad (1)$$

to be $$\Delta t = (2Wo)^2/6D \quad (2)$$

Consequently, the speed at which the target particles move by Brownian movement (diffusion movement speed) Vdif can generally be expressed as follows:

$$V\text{dif} = 2Wo/\Delta t = 3D/Wo \quad (3)$$

Therefore, the movement speed during movement of the location of the photodetection region is set to a value that is sufficiently faster than that speed by referring to Vdif. For example, in the case the diffusion coefficient D of an observation target particle is predicted to be about $2.0 \times 10^{-10}$ m²/s and Wo is about 0.62 μm, since Vdif becomes $1.0 \times 10^{-3}$ m/s, the movement speed of the location of the photodetection region is set to a value of 15 mm/s, that is about 10 times greater than that. Furthermore, in the case the diffusion coefficient of a target particle is unknown, a movement speed of the location of the photodetection region can be determined by repeatedly carrying out preliminary experiments in order to find those conditions under which the prolife of changes in light intensity become the predicted profile (and typically, a prolife that is roughly the same as the excitation light distribution) by trying various settings for the movement speed of the location of the photodetection region.

Disturbances such as flow or vibrations in the sample solution should be minimized in order to stabilize other properties of the luminescent particles. Thus, the location of the photodetection region may be moved by changing the light path of the optical system of a microscope as a general rule. This is because, as was previously explained, the location of the photodetection region can be moved at a high speed comparatively easily by changing the light path with the mirror light deflector 17.

With respect to this point, the peripheral edge of the field of an object lens generally exhibits considerable aberration, and since there is the possibility of this changing depending on the dimensions and shape of the photodetection region, the range of movement of the location of the photodetection region by changing the light path may be made to be within a region close to the center of the field of the object lens where there is little aberration.

On the other hand, if the range of movement of the location of the photodetection region is limited to a region close to the center of the field of the object lens, the region through which the photodetection region passes, namely the scanning region, becomes smaller and the number of luminescent particles able to be detected decreases. In addition, in the case of repeatedly passing through a small region, the photodetection region ends up repeatedly passing through regions where particles are present, particularly with respect to slowly diffusing particles, thereby resulting in the same particle being detected multiple times. Although it is also useful to accurately estimate the properties of light by intentionally repeatedly detecting light from the same particle, when desiring to increase the number of detections of luminescent particles as much as possible such as when counting the number of luminescent particles or detecting their concentration or number density, a region having a wider range or a greater distance may be scanned rather than detecting the same particle multiple times. In addition, when desiring to obtain information such as luminescent particle concentration at that time, it may be made easy to estimate the length or volume of the scanned region (region through which the photodetection region passes) without there being hardly any changes in the dimensions or shape of the photodetection region.

Movement of the location of the photodetection region is made to be such that a wider region or greater distance can be stably scanned by moving the location of the photodetection region on a prescribed scanning track, and ensuring that the location of the photodetection region does not pass the same region (excluding path intersections) as much as possible within a short period of time. The movement path of the location of the photodetection region may be three-dimensional or two-dimensional.

Namely, the location of the photodetection region is moved along a second path over which the location of the first path moves in the sample solution. According to this configuration, as a result of the location of the second path along which the location of the photodetection region moves being moved, the movement path of the location of the photodetection region in the sample solution (excluding cases in which the paths momentarily intersect) does not pass through the same region at least until movement of the location of the second path along the first path is completed, thereby greatly reducing the possibility of detecting a luminescent particle two or more times. In addition, as a result of the location of the photodetection region being moved in the sample solution, changes in the shape and dimensions of the location of the photodetection region are held to a minimum.

In order to minimize changes in the shape and dimensions of the photodetection region as much as possible, the location of the photodetection region should be restricted to a range of little aberration within the field of the object lens. On the other hand, since the target consists of randomly moving luminescent particles, the location of the photodetection region is allowed to pass through the same location provided an adequate amount of time has elapsed since a detected luminescent particle has moved to a different location. Therefore, the second path serving as the track of the location of the photodetection region and the first path serving as the track of the location of the second path are respectively circulation paths. More specifically, the second path may be, for example, circular or elliptical. On the other hand, the shape of the first path may be circular, elliptical or linear. In such cases, the track of the location of the photodetection region using the sample solution as a reference is easily determined, and since this facilitates confirmation that the location of the photodetection region does not continuously pass through the same region within a short period of time, the movement cycle of the location of the photodetection region along the second path is set to be shorter than the movement cycle of the location of the second path along the first path.

Figure 2C:
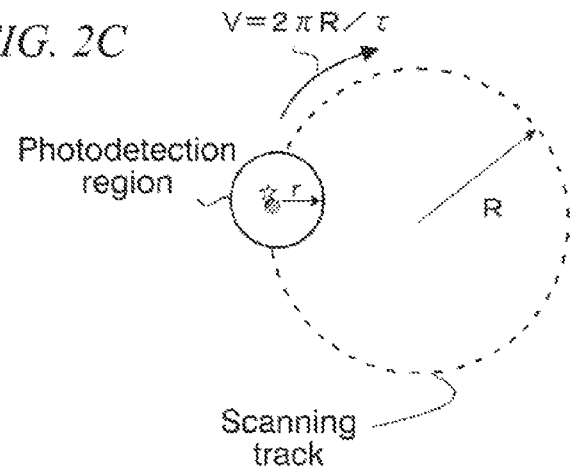
FIG. 2C is a drawing for explaining a mode of movement of the location of a photodetection region along a scanning track (second path) by changing the light path of an optical system in the present embodiment.
Figure 2D:
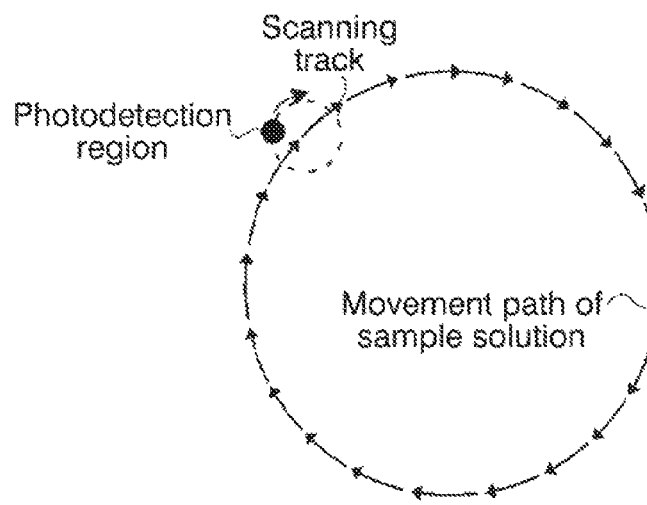
FIG. 2D is a drawing for explaining a mode of movement of the location of a sample solution (movement of the location of a second path along a first path).

More specifically, the mirror light deflector 17 of FIG. 1A is first driven to change the light path, and the photodetection region is made to circle along the scanning track (second path) in the field of the object lens as shown in FIG. 2C. Simultaneous to this movement, the stage position adjustment device 17a is continuously driven, and as a result thereof, the position of the scanning track of the photodetection region is moved based on the sample solution as shown in FIG. 2D to avoid as much as possible causing the photodetection region to scan the same region within a short period. (As shown in FIG. 2D, if the movement of the location of the sample solution is made to follow a circulation path, although the photodetection region again scans the same region when the location of the scanning track of the photodetection region completes one revolution of that circulation path, since luminescent particles are normally assumed to move to a different location by diffusion during the time the location of the scanning track of the photodetection region makes one revolution, the likelihood of repeatedly detecting the same luminescent particle is considered to be extremely low.)

Figure 2E:
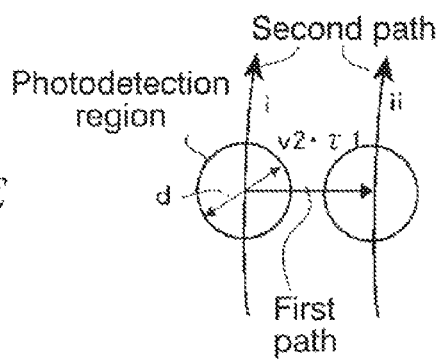
FIG. 2E is a drawing for explaining the relationship between movement of the location of a sample solution and movement of the location of a photodetection region along a scanning track.

Furthermore, although it is desirable that the speed of the photodetection region based on the sample solution be roughly constant so that the pulsed shape of light signals of luminescent particles is constant at all times, if the movement speed of the location of the sample solution is high to a degree that is comparable to the movement speed of the photodetection region on the scanning track, the speed of the photodetection region based on the sample solution fluctuates. Therefore, the movement speed of the location of the sample solution may be sufficiently low (for example, 20% or less) in comparison with the movement speed of the photodetection region on the scanning track. In addition, as shown in FIG. 2E, in order to avoid overlapping between the region passed through during the previous revolution (i) and the region passed through during the current revolution (ii) when the photodetection region circles the scanning track, the movement speed of the location of the sample solution (movement speed of the location of the scanning track) v2 and the movement cycle τ1 of the photodetection region on the scanning track for a diameter d of the photodetection region are set so as to satisfy the relational expression indicated below.

$$v2 \cdot \tau1 > d \quad (4)$$

As a result, since the second path at least moves over a distance equivalent to the diameter of the photodetection region during the time the location of the photodetection region makes one revolution along the second path, overlapping of the photodetection region with the region passed through during the previous revolution is avoided during continuous circling by the location of the photodetection region. More specifically, if the diameter d of the photodetection region is assumed to be 0.4 μm to 30 μm and the movement cycle τ1 of the photodetection region on the scanning track is assumed to be 0.6 msec to 600 msec, then the movement speed v2 of the location of the sample solution becomes 0.67 μm or more. In actuality, since the movement cycle τ1 of the photodetection region on the scanning track is normally set to 6 msec to 60 msec, the movement speed v2 of the location of the sample solution in that case becomes 17 μm or more. Since the movement speed of the photodetection region on the scanning track is typically set to 10 mm/sec to 90 mm/sec, the movement speed v2 of the location of the sample solution is nearly small enough to be able to be ignored.

More specifically, movement of the location of a photodetection region in a sample solution in the optical system of a confocal optical microscope can be carried out by either changing the light path of the optical system of the microscope or by moving a container containing the sample solution. Therefore, movement of the location of the photodetection region along the second path may be carried out by changing the light path of the optical system of a microscope, while movement of the location of the second path along the first path may be carried out by moving the location of the sample solution. In other words, according to this mode, by combining circling movement of the photodetection region by changing the light path of the optical system with circling movement of the sample solution, the sample solution can be scanned over a wider range or over a greater distance. Here, movement of the location of the photodetection region in the sample solution along the second path by changing the light path of the optical system of a microscope may be carried out by any arbitrary method. For example, the location of the photodetection region may be changed by changing the light path of the optical system of a microscope by using a galvanometer mirror and the like employed in laser scanning optical microscopes. According to a mode in which the location of the photodetection region is changed by changing the light path of the optical system of a microscope, since movement of the photodetection region is rapid and there is substantially no occurrence of mechanical vibrations or actions attributable to fluid dynamics in the sample solution, light can be measured in a stable state in which luminescent particles targeted for detection are unaffected by dynamic action, thereby making this advantageous. More specifically, the second path may be circular or elliptical. On the other hand, the shape of the first path may be circular, elliptical or linear. Furthermore, movement of the sample solution may consist of moving the sample solution for each sample solution container, such as by moving the microscope stage as previously described. In this case, effects of the sample solution on luminescent particles are reduced since there is no generation of flow in the solution.

<Analysis of Light Intensity by Scanning Molecule Counting Method>

Once chronological light intensity data of a sample solution has been obtained according to the aforementioned processing, the computer 18 carries out processing in accordance with a program stored in a memory device (consisting of a procedure for individually detecting light signals corresponding to individual luminescent particles from detected light), and an analysis of light intensity is carried out in the manner described below.

(i) Detection of Single Target Particle

Figure 6A:
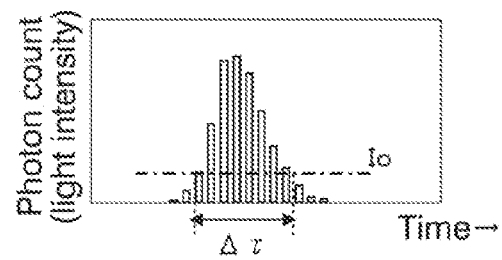
FIG. 6A is an example of a drawing showing an example of chronological changes in photon count (light intensity) measured according to a scanning molecule counting method.

In chronological light intensity data, in the case the locus when a single target particle passes through a photodetection region is roughly linear in the manner shown in FIG. 4A, the change in light intensity corresponding to that particle has a profile (normally, a roughly bell-shaped profile) that reflects the distribution of light intensity in the photodetection region (determined according to the optical system) as schematically depicted in FIG. 6A. Therefore, in one technique for detecting target particles, a threshold value Io is set for light intensity, and when a duration Δτ during which light intensity continuously exceeds that threshold value is within a prescribed range, that profile of light intensity is judged to correspond to the passage of a single particle through the photodetection region, and that single target particle is detected. The threshold value Io of light intensity and the prescribed range of duration Δτ are determined based on a profile presumed to be the intensity of light emitted from a conjugate of a target particle and luminescent probe (or a luminescent probe that has been degraded and separated after binding with that particle) that moves at a prescribed speed relative to the photodetection region. Specific values may be arbitrarily set experimentally, or may be selectively determined according to the properties of the conjugate of the target particle and luminescent probe (or a luminescent probe that has been degraded and separated from the particle after binding with that particle).

In addition, in another technique for detecting target particles, when the distribution of light intensity of a photodetection region can be assumed to be a Gaussian distribution as indicated below, $$I = A \cdot \exp(-2t^2/a^2) \quad (5)$$

the profile of that light intensity is judged to correspond to the passage of a single target particle through the photodetection region when intensity A and width a as determined by fitting equation (5) to a profile of significant light intensity (profile able to be clearly determined to not be background) are within prescribed ranges, and a single target particle is detected. (The profile is ignored as constituting noise or artifact during analysis when intensity A and width a are outside the prescribed ranges.)

(ii) Counting of Target Particles

Counting of target particles is carried out by counting the number of particles detected according to the aforementioned techniques for detecting target particles by an arbitrary method. However, in the case of a large number of particles, counting may be carried out according to processing exemplified in FIGS. 5 and 6B.

Figure 5:
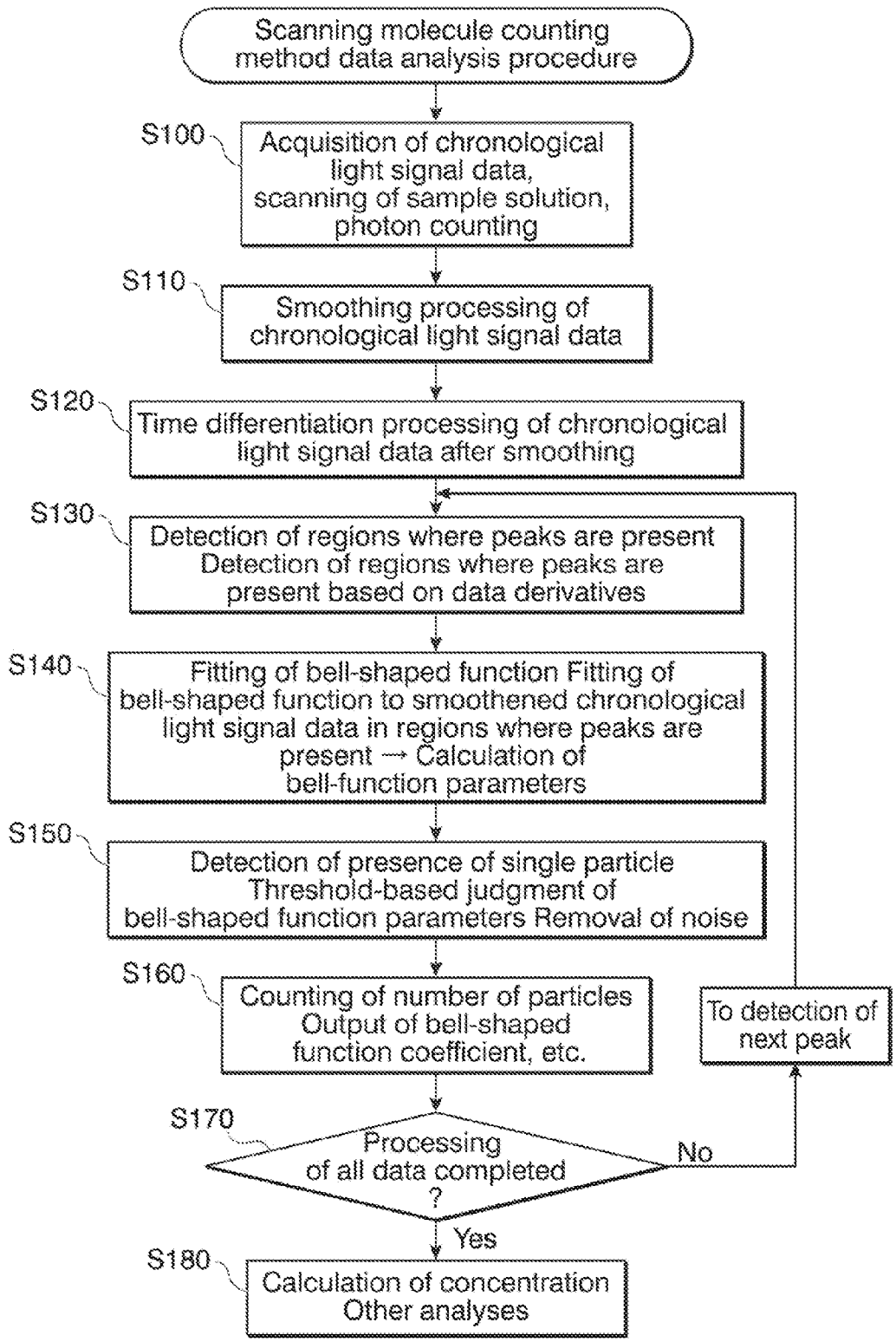
FIG. 5 is a drawing indicating a processing procedure in the form of a flow chart for counting particles based on chronological changes in a photon count (light intensity) measured according to a scanning molecule counting method.
Figure 6B:
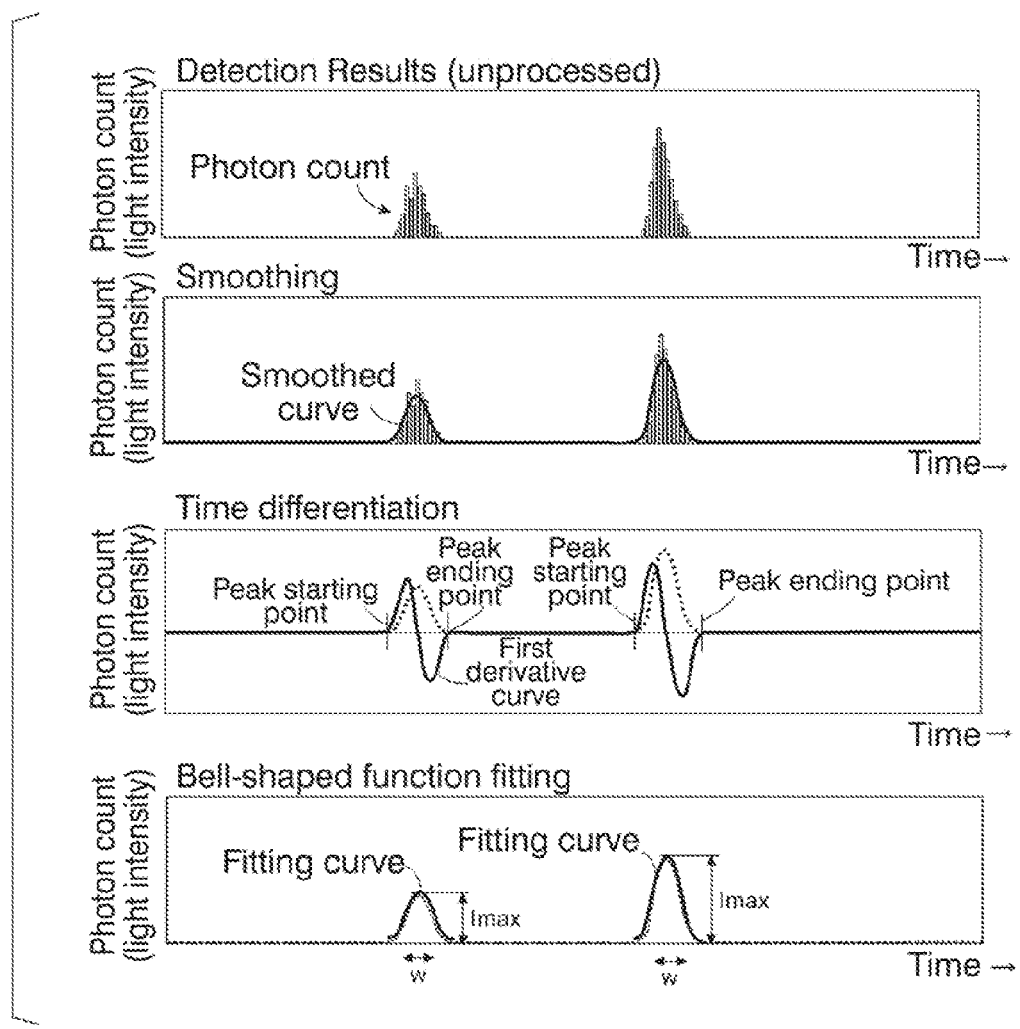
FIG. 6B is a drawing explaining an example of a signal processing of a detection signal in a processing procedure for counting particles based on chronological changes in a photon count (light intensity) measured according to a scanning molecule counting method.

With reference to FIGS. 5 and 6B, in one example of a method for counting particles from chronological light intensity (photon count) data, after having acquired chronological light signal data (photon count data) by carrying out measurement of light intensity explained above, namely by carrying out scanning of a sample solution by photodetection regions and counting the number of photons (S100), smoothing processing (S110, "Smoothing" in the mid-upper row of FIG. 6B) is carried out on the chronological light signal data ("Detection result (unprocessed)" in the top graph of FIG. 6B). Since light emitted from conjugates of the particles and luminescent probe or that emitted from the luminescent probe is released statistically, thereby resulting in the possibility of omission of data values for minute time periods, this smoothing processing makes it possible to ignore omission of data values as described above. Smoothing processing is carried out by, for example, the moving average method. Furthermore, parameters used when carrying out smoothing processing, such as the number of data points averaged at one time, or the number of times movement is averaged in the case of the moving average method, are suitably set corresponding to the movement speed of the location of the photodetection region when acquiring light signal data (scanning speed) and bin time.

Next, in order to detect a time region in which a significant signal is present (peak region) in chronological light signal data following smoothing processing, a first derivative is calculated for the time of the chronological light signal data following smoothing processing (S120). Since the change in the time derivative of chronological light signal data increases at the inflection point of the signal value as exemplified by "Time differentiation" in the mid-low of FIG. 6B, the starting point and ending point of a significant signal (peak signal) can be advantageously determined by referring to this time derivative.

Subsequently, significant signals (peak signals) are chronologically detected in the chronological light signal data, and a judgment is made as to whether or not the detected peak signals are signals corresponding to target particles.

Figure 7:
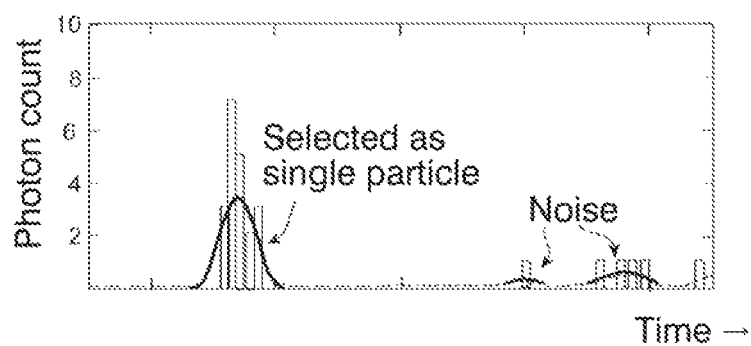
FIG. 7 indicates an example of actual measurements of photon counting data measured according to a scanning molecule counting method (bar graph), a curve obtained by smoothing the data (dotted line), and a Gaussian function fit to those regions where peaks are present (solid line), and in the drawing, signals indicated as being "noise" are ignored as signals attributable to noise or artifacts.

More specifically, a peak region is identified by seeking and determining the starting point and ending point of a single peak signal by chronologically referring to time derivatives in the chronological time-differentiated data of the chronological light signal data (S130). Once a single peak region has been identified, a bell-shaped function is fit to the smoothened chronological light signal data in that peak region (Bell-shaped function fitting" in the bottom graph of FIG. 6B), and parameters such as peak intensity Imax of the bell-shaped function, peak width (half width at maximum) w and correlation coefficient (of the least squares method) during fitting are calculated (S140). Furthermore, although the bell-shaped function subjected to fitting is typically a Gaussian function, it may also be a Lorentzian function. A judgment is then made as to whether or not the calculated bell-shaped function parameters are within a presumed range for the parameters of a bell-shaped profile depicted by a light signal detected when a single conjugate of a particle and luminescent probe or luminescent probe has passed through a photodetection region, namely whether or not peak intensity, peak width and correlation coefficient are each within a prescribed range (S150). Thus, in the case of a signal for which calculated bell-shaped function parameters have been judged to be within the presumed range for a light signal corresponding to a single conjugate of a particle and luminescent probe or luminescent probe as indicated on the left side of the graph of FIG. 7, that signal is judged to be a signal corresponding to a single target particle, and as a result, a single target particle is judged to have been detected and that target particle is counted as a single particle (and the particle count is incremented by 1, S160). On the other hand, in the case of peak signals in which the calculated bell-shaped function parameters are not within the presumed range as indicated on the right side of the graph of FIG. 7, those signals are ignored as constituting noise.

The searching and assessment of peak signals in the aforementioned processing of S130 to S160 are carried out repeatedly for the entire range of chronological light signal data, and each time a single target particle is detected, that target particle is counted as a particle. When searching for peak signals throughout the entire range of chronological light signal data has been completed (S170), the particle count value obtained up to that time is taken to be the number of target particles detected in the chronological light signal data.

(iii) Determination of Number Density or Concentration of Target Particles

When target particles are counted, the number density or concentration of the target particles is determined using the total volume of the photodetection region traversed by the target particles during acquisition of chronological light signal data. However, since the effective volume of the photodetection region fluctuates dependent upon the wavelength of the excitation light or detection light, numerical aperture of the lens, and adjusted state of the optical system, it is generally difficult to determine the number density or concentration of target particles from design values, and thus it is not easy to determine the total volume of the traversed region of a photodetection region. Therefore, light intensity is typically measured and particles are detected and counted as previously explained for a solution having a known particle concentration (reference solution) under the same conditions as those used when measuring a sample solution to be tested, and the total volume of the traversed photodetection region, namely the relationship between the detected number and concentration of target particles, is determined from the number of detected particles and the particle concentration of the reference solution. The particles of the reference solution may consist of a fluorescent label (such as a fluorescent dye) having luminescent properties similar to conjugates of the particles and luminescent probe formed by the target particles (or luminescent probe that has separated after binding with the target particles). More specifically, when assuming a number of detected particles N for a reference solution having a particle concentration C, for example, then the total volume Vt of the traversed region of the photodetection region is given by the following equation:

$$Vt = N/C \quad (6)$$

In addition, a plurality of solutions having different concentrations may be provided for use as reference solutions, measurements may be carried out on each reference solution, and the average value of the calculated Vt may be used as the total volume Vt of the traversed region of the photodetection region. If Vt is given, then the number density c of particles in a sample solution for which the result of particle counting is n is given by the following equation:

$$c = n/Vt \quad (7)$$

Furthermore, determination of the volume of a photodetection region and the total volume of the traversed photodetection region is not limited to the aforementioned method, but rather may also be obtained by an arbitrary method such as FCS or FIDA. In addition, the optical analysis device of the present embodiment may preliminarily store information on the relationship between concentration C and particle count N (Equation (6)) for various standard particles and for presumed photodetection region movement patterns in a memory device of the computer 18, and may be configured so that a device user is able to use that suitably stored relationship information when performing optical analyses.

<Target Particle Detection Method>

The method for detecting a target particle of the present embodiment is a method for detecting a target particle dispersed and randomly moving in a solution, wherein after separating and removing free luminescent probe not bound to the target particle from luminescent probe bound to the target particle, the target particle bound to the luminescent probe is detected by the scanning molecule counting method. Since the scanning molecule counting method is a measurement method that enables luminescent particles to be measured one particle at a time while molecules are in a discrete state, measurements can be carried out on luminescent particles at a comparatively low concentration on the pM order or lower. Consequently, even in cases in which the concentration of target particles to be analyzed in a sample solution is extremely low, the method for detecting a target particle of the present embodiment can be used to count a target particle bound to a luminescent probe with high sensitivity. Moreover, in the method for detecting a target particle of the present embodiment, a particle for separation and recovery is recovered by solid-liquid separation treatment after a target particle labeled with a luminescent probe is bound to the particle for separation and recovery, and the recovered particle for separation and recovery is measured according to the scanning molecule counting method. Since a target particle labeled with the luminescent probe is recovered together with the particle for separation and recovery since the target particle labeled with the luminescent probe is bound to the particle for separation and recovery, free luminescent probe not bound to the target particle is separated from the particle for separation and recovery and removed. Namely, since measurement is carried out according to the scanning molecule counting method after having removed free luminescent probe not bound to the target particles, detection of light from the free luminescent probe is effectively inhibited, thereby enabling the target particles to be detected with high accuracy.

More specifically, the method for detecting a target particle of the present embodiment comprises the following (a) to (c):

(a) preparing a solution containing a target particle, a luminescent probe that binds to the target particle and a particle for separation and recovery that is capable to be bound to a complex composed of the target particle and the luminescent probe, or containing the target particle bound to the luminescent probe, the luminescent probe and the particle for separation and recovery, and forming a complex comprising the target particle, the luminescent probe and the particle for separation and recovery in the solution, (b) recovering the particle for separation and recovery from the solution by solid-liquid separation treatment after step (a), and preparing a sample solution containing the particle for separation and recovery, and (c) calculating the number of the complex present in the sample solution prepared in the (b), thereby detecting the target particle.

The following provides an explanation of (a) to (c).

First, in the (a), a solution containing a target particle, a luminescent probe that binds to the target particle and a particle for separation and recovery that is capable to be bound to a complex composed of the target particle and the luminescent probe, or containing the target particle bound to the luminescent probe, the luminescent probe and the particle for separation and recovery, is prepared, and a complex comprising the target particle, the luminescent probe and the particle for separation and recovery is formed in the solution.

In the present embodiment and description of the present application, "a particle dispersed and moving randomly in a sample solution" refers to a particle such as an atom, a molecule or an aggregate thereof dispersed or dissolved in a solution (and may be a particle that emits light or a particle that does not emit light) that moves about freely by Brownian movement in a solution without being immobilized on a substrate and the like.

The target particle refers to a particle targeted for detection that is dispersed and moving randomly in a solution. Examples of the target particle includes a biomolecule such as a protein, a peptide, a nucleic acid, a nucleic acid-like substance, a lipid, a saccharide, an amino acid or an aggregate thereof, a particulate biological target such as a virus or a cell, and a non-biological particle (such as an atom, a molecule, a micelle or a metal colloid). The Nucleic acid may be DNA or RNA, or may be an artificially amplified substance in the manner of cDNA. Examples of the nucleic acid-like substance include substances in which side chains and the like of naturally-occurring nucleotides in the manner of DNA or RNA (nucleotides present in nature) have been modified by functional groups such as an amino group, and substances that have been labeled with a protein or low molecular weight compound and the like. Specific examples of nucleic acid-like substances include bridged nucleic acids (BNA), nucleotides in which an oxygen atom at position 4' of a naturally-occurring nucleotide has been substituted with a sulfur atom, nucleotides in which a hydroxyl group at position 2' of a naturally-occurring nucleotide has been substituted with a methoxy group, hexitol nucleic acids (HNA) and peptide nucleic acids (PNA).

In addition, a luminescent probe used in the present embodiment is a substance that specifically or non-specifically binds or adsorbs to a target particle, and there are no particular limitations thereon provided it is a substance that releases light when bound to a target particle. In addition, binding between the luminescent probe and target particle may be reversible or irreversible such as in the manner of a covalent bond. For example, the luminescent probe may be a substance in which a fluorescent substance is bound to a substance that specifically or non-specifically binds or absorbs to a target particle. Although the luminescent substance is typically a fluorescent substance, it may also be a substance that emits light by phosphorescence, chemiluminescence, bioluminescence or light scattering. There are no particular limitations on the fluorescent substance provided it is a substance that releases fluorescence as a result of being irradiated with light of a specific wavelength, and can be used by suitably selecting from among fluorescent dyes used in FCS or FIDA and the like.

For example, in the case the target particle is a nucleic acid or nucleic acid-like substance, examples of the luminescent probe include a substance in which a luminescent substance such as a fluorescent substance is bound to an oligonucleotide that hybridizes with the target particle, a nucleic acid-binding protein bound with a luminescent substance such as a fluorescent substance, and a dye molecule that binds to nucleic acid. The oligonucleotide may be DNA, RNA or an artificially amplified substance in the manner of cDNA, or a substance that contains a portion or all of a nucleic acid-like substance capable of forming a nucleotide chain and base pairs in the same manner as naturally-occurring nucleic acid bases. In addition, in the case the target particle is a protein or low molecular weight compound and the like, an antigen or antibody to the target particle, a ligand or receptor for the target particle, or a substance that specifically binds to a target particle in the manner of biotin and avidin, which is labeled with a luminescent substance such as a fluorescent substance, can be used as a luminescent probe. Furthermore, binding of a luminescent substance to a substance that specifically or non-specifically binds or absorbs to a target particle such as a nucleic acid or protein can be carried out by ordinary methods.

The luminescent probe used in the present embodiment may itself be a luminescent substance capable of binding to a target particle by a synthesis reaction and the like. For example, a functional group in a luminescent substance such as a fluorescent substance may be bound to a functional group in a target particle by various types of synthesis reactions. Examples of these synthesis reactions include an EDAC (1-ethyl-3-(3-dimethylaminopropyl)-carbodiimide hydrochloride) reaction in which carboxylic acid and an amino group are bound with a water-soluble carbodiimide, a reaction in which carboxylic acid and an amino group are bound by preliminarily mixing 1-ethyl-3-(3-dimethylaminopropyl) carbodiimide hydrochloride (EDC) and N-hydroxysuccinimide (NHS), and a reaction in which an activated aldehyde group or tosyl group bonds to a functional group in a target particle. In addition, the synthesis reaction may also be a reaction in which an amino group in a target particle is crosslinked with an amino group in a luminescent substance using a dipolar linker.

Although the luminescent probe used in the present embodiment may be that which non-specifically binds to a target particle, from the viewpoint of accuracy of detection and quantitative determination of target particles, a substance may be that which binds specifically thereto. Furthermore, the luminescent probe that specifically binds to a target particle is only required to be a substance that preferentially binds to the target particle rather than binding to other substances having physical or chemical properties similar to those of the target particle, and is not required to be a substance that does not bind at all to substances other than the target particle. For example, in the case the target particle is a nucleic acid, an oligonucleotide labeled with a luminescent substance used as a luminescent probe may have a base sequence that is completely complementary to the base sequence of the target particle, or may have a base sequence that contains mismatches with the base sequence of the target particle.

In the present embodiment, the majority of free luminescent probe not bound to a target particle (luminescent probe present alone) is removed from the sample solution used in measurement according to the scanning molecule counting method. Consequently, even if the luminescent probe in a state of being bound to a target particle and luminescent probe in a state of being present alone have the same luminescence properties, the target particles can be detected with high accuracy.

In the present embodiment, a luminescent probe may be used for which luminescence properties of light released therefrom differ between the state in which the luminescent probe is bound to a target particle and the state in which the luminescent probe is present alone. As a result of making the intensity of light of a specific wavelength to be different between the state in which the luminescent probe is present alone and the state in which the luminescent probe is bound to a target particle (such as by causing fluorescence intensity to differ), target particles can be detected with high accuracy. Furthermore, a luminescent probe having different luminescence properties between the state in which it is bound to a target particle and the state in which it is present alone means that the intensity of light of specific wavelength differs between the state in which it is bound to a target particle and the state in which it is present alone.

For example, in the case the target particle is a protein, a dye (such as a fluorescent dye in the manner of hydrophobic probes ANS, MANS and TNS) can be used as a luminescent probe that undergoes a change in fluorescence intensity or fluorescence wavelength due to a change in the ambient environment as a result of binding with the protein. In addition, the luminescent probe per se is not necessarily required to emit light. For example, in the case the target particle is a nucleic acid or nucleic acid-like substance, by using an oligonucleotide that hybridizes with the target particle as a luminescent probe, luminescence properties can also be made to differ between the state in which the luminescent probe is present alone and the state in which the luminescent probe is bound to the target particle by binding a fluorescent double-stranded nucleic acid-like substance, which specifically binds to a double-stranded structure, to an association product composed of a target particle and luminescent probe. Examples of fluorescent double-stranded nucleic acid-like substances that specifically bind to a double-stranded structure include fluorescent intercalators and groove binders bound to a fluorescent substance.

In addition, substances composed of at least two constituents that emit fluorescence due a mutual positional change in at least one of the two constituents, for example, may also be employed as luminescent probes. Examples of such substances include fluorescent proteins that undergo a structural change and release strong fluorescence when binding to a certain particle, and molecules that aggregate to form a fluorescent metal complex when binding to a certain molecule (complex ligands). According to this configuration, since a luminescent probe alone or a luminescent probe that does not bind to a target particle either does not emit hardly any light, or even if it emits light, since the wavelength differs from that of a conjugate of the target particle and luminescent probe, light from the conjugate of the target particle and luminescent probe can be selectively detected.

In addition, luminescence properties can also be made to differ between a luminescent probe that is present alone and a luminescent probe in a state of being bound to a target particle by using fluorescence resonance energy transfer (FRET). For example, a substance serving as an energy donor and a substance serving as an energy acceptor in FRET (a fluorescent substance and a quencher substance) can be used as substances that bind to a target particle, and a substance for which FRET occurs in a state in which a luminescent probe is present alone but for which FRET is not allowed to occur in the state of being bound to the target particle can be used as a luminescent probe. Since FRET does not occur from the luminescent probe bound to the target particle, fluorescence is released from the fluorescent substance serving as the energy donor. On the other hand, fluorescence released from the fluorescent substance serving as the energy donor is either not detected from the fluorescent probe present alone or that fluorescence is weak. Therefore, by detecting fluorescence released from the fluorescent substance serving as the energy donor, a target particle bound to the luminescent probe can be distinguished from the luminescent probe present alone and thereby detected.

For example, in the case the target particle is a nucleic acid or nucleic acid-like substance, a fluorescent substance serving as an energy donor and a substance serving as an energy acceptor in FRET may be used as oligonucleotides that form an intramolecular structure when in the state of a single-stranded nucleic acid, and a molecular beacon probe bound such that FRET occurs when in the state of a single-stranded nucleic acid molecule, but does not occur when in the state of an association product formed by hybridizing with another single-stranded nucleic acid molecule, may be used as a luminescent probe. For example, a substance may be used that has a fluorescent substance serving as an energy donor or a substance serving as an energy acceptor bound to the 3'-terminal side with the remaining other of the pair bound to the 5'-terminal side, has base sequences that are mutually complementary to the region of 5'-terminal side and 3'-terminal side, and forms an intramolecular structure (a so-called stem-loop structure) by forming base pairs in these base sequences. Furthermore, the mutually complementary regions that form the intramolecular base pairs of the molecular beacon probe are present so as to interpose a region that hybridizes with a target particle, and the region on the 3'-terminal side and the region on the 5'-terminal side may be regions that respectively contain the 3'-terminal or 5'-terminal or regions that do not. In addition, the number of bases and base sequence of the regions that form the base pairs are to such a degree that the stability of the formed base pairs is lower than the stability of the association product with the target particle, and base pairs can be formed under the measurement conditions.

In addition, in the case the target particle is a nucleic acid or nucleic acid-like substance, a luminescent probe present alone can also be distinguished from a luminescent probe bound to a target particle by using a fluorescent double-stranded nucleic acid-binding substance that specifically binds to a double-stranded structure and inducing FRET between the fluorescent double-stranded nucleic acid-binding substance and a fluorescent substance labeled with the luminescent probe. Namely, one of either a fluorescent double-stranded nucleic acid-binding substance or a fluorescent substance labeled with the luminescent probe serves as a FRET energy donor while the other serves as a FRET energy acceptor. Fluorescence released from the fluorescent substance labeled with the luminescent probe is detected from the luminescent probe present alone. In contrast, since the fluorescent double-stranded nucleic acid-binding substance binds to the luminescent probe bound to a target particle, fluorescent released by FRET is detected, and as a result thereof, it can be distinguished from the luminescent probe present alone, thereby enabling its detection.

Furthermore, in the case the amount of fluorescent intercalator inserted between the base pairs of the association product of the luminescent probe and target particle is excessively large, the background level when detecting fluorescence released by FRET becomes excessively high, resulting in the risk of having an effect on detection accuracy. Consequently, the luminescent probe may be designed so that the region that forms a double-strand in the association product of the luminescent probe and target particle is 400 bp or less.

In addition, two types of luminescent probes may also be used in the present embodiment. For example, in the case the target particle is a nucleic acid or nucleic acid-like substance, two types of luminescent probes are designed to as to hybridize mutually adjacent to a target particle, one of the luminescent probes is labeled with a fluorescent substance serving as an energy donor in FRET, and the other luminescent probe is labeled with a substance serving as an energy acceptor in FRET. In this case, although FRET does not occur in the case the luminescent probe is present alone, as a result of binding to the target particle, the two types of luminescent probes are mutually brought into close proximity thereby resulting in the occurrence of FRET. Consequently, the target particle bound to the luminescent probe can be detected by detecting fluorescence released by FRET.

In the case the target particle is a nucleic acid or nucleic acid-like substance, light may be made to be released from a luminescent probe bound to the target particle by using two types of luminescent probes and utilizing a quenched autoligation (QUAL) reaction (J. Am. Chem. Soc., 2002 (10), p. 2096).

More specifically, two probes are prepared by designing a nucleic acid probe that hybridizes with the target particle and has a special 3'-terminal modifying group (N probe), and a nucleic acid probe that hybridizes with the target particle adjacent to the 3'-terminal side of the N probe and is modified with a quenching dye and fluorescent dye on the 5'-terminal side thereof (E probe). When the two probes hybridize with the target particle, a non-enzymatic ligation (autoligation) reaction occurs, and the quenching dye leaves the E probe at this time. In other words, the two probes only emit fluorescence when hybridized with the target particle.

The particle for separation and recovery used in the present embodiment specifically or non-specifically binds or absorbs to a conjugate of the target particle and luminescent probe, can be suspended in water, and can be separated from a liquid by ordinary solid-liquid separation treatment. For example, a particle that can be suspended in water, and is obtained by binding a substance that specifically or non-specifically binds or adsorbs to the target particle with a particle that can be separated from liquid by ordinary solid-liquid separation treatment, can be used as a particle for separation and recovery. In addition, a particle that has a site on the surface thereof that does not bind with luminescent probe not bound to the target particle but is able to bind with luminescent probe bound to the target particle, can be suspended in water, and can be separated from liquid by ordinary solid-liquid separation treatment, may also be used.

The particle for separation and recovery is required to maintain a suspended state in a sample solution during measurement according to the scanning molecule counting method. This is because a particle that precipitates in the sample solution during measurement is difficult to detect accurately by the scanning molecule counting method. Consequently, the sedimentation rate of the particle for separation and recovery used in the present embodiment in a sample solution can be $1\times10^{-6}$ m/s or less and can also be $1\times10^{-7}$ m/s or less.

Furthermore, particle sedimentation rate is typically determined according to the Stokes' equation. In the following equation (8), r represents bead radius, $\rho_p$ represents bead density, $\rho_f$ represents solution density, g represents gravitational acceleration, and η represents solution viscosity.

$$v_s = \frac{2}{9}\frac{r^2(\rho_p - \rho_f)g}{\eta} \quad (8)$$

Particles used for the particles for separation and recovery can be suitably selected and used from among particles commonly used for treatment such as substance purification and separation in the relevant technical field provided they are particles that can be suspended in water and can be separated from liquid by ordinary solid-liquid separation treatment. The particles for separation and recovery used in the present embodiment may be magnetic particles or non-magnetic particles. In addition, the particles for separation and recovery may be biomaterials such as viruses, bacteria or cells. The particles for separation and recovery used in the present embodiment may be particles composed of one type of material or may be particles composed of two or more types of materials. Moreover, one type of particle for separation and recovery may be used or two or more types of particles for separation and recovery may be used as a mixture.

Examples of magnetic particles include particles composed of a metal such as triiron tetraoxide ($Fe_3O_4$), diiron trioxide (γ-$Fe_2O_3$), various types of ferrite, iron, manganese, nickel, cobalt or chromium, and particles composed of an alloy containing cobalt, nickel or manganese. In addition, the magnetic particles may be particles composed only of a magnetic substance or particles that contain fine particles of a magnetic substance within non-magnetic particles. Examples of non-magnetic particles include latex particles composed of a hydrophobic polymer, and latex particles composed of a crosslinked hydrophilic polymer. The non-magnetic particles may also be latex particles composed of a copolymer of about two to four types of monomers. Examples of hydrophobic copolymers include polystyrene, polyacrylonitrile, polymethacrylonitrile, poly(methyl methacrylate), polycaproamide and polyethylene terephthalate.

In addition, examples of the crosslinked hydrophilic polymers include polyacrylamide, polymethacrylamide, polyvinylpyrrolidone, polyvinyl alcohol, poly(2-oxyethylacrylate), poly(2-oxyethylmethacrylate), poly(2,3-dioxypropylacrylate), poly(2,3-dioxypropylmethacrylate), polyethylene glycol methacrylate and dextran. In addition, the non-magnetic particles may also be particles having fine particles of a magnetic substance immobilized on the surface of non-magnetic particles such as latex particles.

Examples of non-magnetic particles include particles composed of glass, ceramics, plastic or latex. The non-magnetic particles may also be metal particles not having magnetic properties, such as particles composed of aluminum, nickel, alumina, titania or zirconia.

Magnetic particles, glass particles, or particles obtained by binding a substance that specifically or non-specifically binds or adsorbs to target particles to latex particles, may be used for the particles for separation and recovery used in the present embodiment. In addition, since solid-liquid separation treatment can be easily carried out by using a magnetic field, the particles for separation and recovery can be magnetic particles. For example, only magnetic particles can be recovered in a container by bringing a magnet in close proximity to the container containing a suspension of magnetic particles, and causing the magnetic particles to converge at the surface of the container in closest proximity to the magnet, followed by removing the supernatant.

There are no particular limitations on the particles for separation and recovery provided they are able to maintain a suspended state in a sample solution during measurement according to the scanning molecule counting method, and their average particle diameter, density and the like can be suitably adjusted in consideration of the material of the particles for separation and recovery used, the viscosity of the sample solution and the like. For example, the average particle diameter of the particles for separation and recovery can be 1 nm to 100 μm and can also be 0.01 μm to 50 μm.

In order to produce the particles for separation and recovery used in the present embodiment, a substance similar to the luminescent probe, such as a substance in the manner of an oligonucleotide that hybridizes with the target particle, an antigen or antibody to the target particle, a ligand or receptor for the target particle, or biotin or avidin, can be used for the substance that can be suspended in water, is bound to particles that can be separated from liquid by an ordinary solid-liquid separation treatment, and specifically or non-specifically binds or adsorbs to the target particle. Furthermore, although the particles for separation and recovery may be those that non-specifically bind to the target particle, they may specifically bind to the target particle from the viewpoints of accurate detection and quantitative determination of the target particle.

There are no particular limitations on the method used to bind the particle able to be suspended in water that can also be separated from liquid by ordinary solid-liquid separation treatment with a substance that specifically or non-specifically binds to a target particle, and may be bound by physical adsorption or the substance may be chemically bound to a functional group on the particle surface. In the case of chemical bonding, bonding can be carried out by a method suitable for each functional group. Examples thereof include an EDAC reaction, a reaction in which carboxylic acid and an amino group are bound by preliminarily mixing EDC and NHS, a reaction in which amino groups are crosslinked using a dipolar linker, and a reaction in which an activated aldehyde group or tosyl group is bond to a functional group in a substance that specifically or non-specifically binds or adsorbs to a target particle. The particle surface may be coated with functional groups in the case of magnetic particles not having functional groups on the particle surface.

More specifically, in the aforementioned (a) in the method of the present invention, a solution containing a target particle, a luminescent probe and a particle for separation and recovery, or containing the target particle bound to the luminescent probe, the luminescent probe and the particle for separation and recovery, is prepared. There are no particular limitations on the solvent added to the target particle and the like for preparing the solution provided it does not inhibit the formation of a complex composed of the target particle, luminescent probe and particle for separation and recovery (to also be referred to as a "tripartite complex"), and can be used by suitably selecting from among buffers commonly used in the relevant technical field. Examples of these buffers include phosphate buffers or Tris buffers such as phosphate-buffered saline (PBS, pH 7.4).

This solution can be prepared by respectively adding the target particle, luminescent probe and particle for separation and recovery to a suitable solvent. There are no particular limitations on the order in which they are added provided a tripartite complex is able to ultimately be formed. More specifically, a tripartite complex may be formed in the prepared solution after having added the target particle, luminescent probe and particle for separation and recovery nearly substantially simultaneously. In addition, a tripartite complex may be formed by adding the particle for separation and recovery after having formed a conjugate composed of the target particle and luminescent probe by adding the target particle and luminescent probe, or a tripartite complex may be formed by adding the luminescent probe after having formed a conjugate composed of the target particle and particle for separation and recovery by adding the target particle and particle for separation and recovery.

In the case of being able to bind the target particle and luminescent probe by only having them present in the same solution, after having prepared a sample solution containing the target particle and luminescent probe, the target particle and luminescent probe can be bound in the sample solution simply by incubating the sample solution for a prescribed amount of time as necessary.

On the other hand, in the case the target particle or luminescent probe is a nucleic acid molecule or nucleic acid-like substance having a double-stranded structure, the target particle and luminescent probe can be associated after having denatured the nucleic acid and the like in the sample solution containing the target particle and luminescent probe. Furthermore, "denaturing a nucleic acid molecule or nucleic acid-like substance" refers to dissociation of base pairs. For example, this refers to dissociating base pairs formed by mutually complementary base sequences in a molecular beacon probe to disassemble an intramolecular structure and form a single-stranded structure, or converting a double-stranded nucleic acid molecule into a single-stranded nucleic acid molecule. Furthermore, in the case the luminescent probe is an oligonucleotide containing a nucleic acid-like substance such as PNA, there are cases in which an association product consisting of the luminescent probe and target particle can be formed without having to carry out a special denaturation treatment even if the target particle was in the form of a double-stranded nucleic acid molecule.

Examples of denaturation treatment include denaturation by high-temperature treatment (heat denaturation) and denaturation by low salt concentration treatment. In the case the denaturation treatment is heat denaturation, the effect on a fluorescent substance or other luminescent substance is comparatively small and the procedure is simple. More specifically, in the case of heat denaturation, nucleic acid molecules and the like in a sample solution can be denatured by subjecting the sample solution to high-temperature treatment. In general, although denaturation can be carried out by holding at a temperature of 90° C. for DNA or 70° C. for RNA for several seconds to about 2 minutes, since the denaturing temperature varies according to the base length of the target particle and the like, the temperature is not limited thereto provided denaturation is possible at that temperature. On the other hand, denaturation by low salt concentration treatment can be carried out by, for example, adjusting the salt concentration of the solution to be sufficiently low by diluting with purified water and the like.

After having carried out denaturation as necessary, the target particle and luminescent probe in the aforementioned solution are associated. In the case of having carried out heat denaturation, the target particle and luminescent probe in the solution can be suitably associated by lowering the temperature of the solution to a temperature that allows specific hybridization between the target particle and luminescent probe. In addition, in the case of having carried out denaturation by low salt concentration treatment, the target particle and luminescent probe in the solution can be suitably associated by raising the salt concentration of the solution to a concentration that allows specific hybridization between the target particle and luminescent probe such as by adding a salt solution.

Furthermore, the temperature at which two single-stranded nucleic acid molecules are able to specifically hybridize can be determined from a melting curve of an association product of the target particle and luminescent probe. A melting curve can be determined by, for example, changing the temperature of a solution containing only the target particle and luminescent probe from a high temperature to a low temperature, and measuring optical absorbance or fluorescence intensity of the solution. The temperature range from the temperature at which the two denatured single-stranded nucleic acid molecules begin to form an association product to the temperature at which the nucleic acid molecules have nearly completely formed an association product can be taken to be the temperature at which both specifically hybridize as determined from the melting curve. The concentration at which two single-stranded nucleic acid molecules specifically hybridize can be determined by similarly determining a melting curve by changing the salt concentration in the solution from a low concentration to a high concentration instead of changing the temperature.

The temperature at which two single-stranded nucleic acid molecules specifically hybridize can generally be substituted for the Tm value (melting temperature). For example, the Tm value of a region of a luminescent probe that hybridizes with a target particle (temperature at which 50% of double-stranded DNA dissociates to single-stranded DNA) can be calculated from base sequence information of the luminescent probe by using commonly used primer/probe design software and the like.

In addition, in order to suppress non-specific hybridization, the temperature of a solution may be lowered comparatively slowly when forming an association product. For example, after having denatured a nucleic acid molecule by making the temperature of a solution to be 70° C. or higher, the liquid temperature of the solution can be lowered at a temperature lowering rate of 0.05° C./second or higher.

In addition, in order to suppress non-specific hybridization, a surfactant, formamide, dimethylsulfoxide or urea and the like may be added to the solution in advance.

Only one type of these compounds may be added or two or more types may be added in combination. The addition of these compounds makes it possible to prevent the occurrence of non-specific hybridization in a comparatively low temperature environment.

In general, in order to efficiently label a target particle, the luminescent probe is required to be in excess with respect to the target particle. Consequently, in the case of forming a conjugate composed of a target particle and luminescent probe by preliminarily adding a target particle and luminescent probe, the target particle bound to the luminescent probe and the luminescent probe are contained in the solution following the formation reaction. Thus, the solution of used in the (a) can also be prepared by adding the particles for separation and recovery to the reaction solution following the binding reaction between the target particle and luminescent probe.

For example, a tripartite complex may be formed by adding particles for separation and recovery to a reaction solution following binding of a fluorescent dye to a target particle by a synthesis reaction such as EDAC and incubating as necessary. In addition, in the case the target particle is a nucleic acid or nucleic acid-like substance, a target particle labeled with both a fluorescent substance and a substance able to bind to particles for separation and recovery is obtained in the form of a PCR product by carrying out PCR using the target particle as a template and using a primer labeled with a fluorescent substance or dNTP labeled with a fluorescent substance and a primer labeled with a substance capable of binding to the particles for separation and recovery. A tripartite complex can also be formed by adding particles for separation and recovery to this PCR reaction solution and incubating as necessary.

Next, in the (b), the particles for separation and recovery are recovered from the solution containing the tripartite complex prepared in the (a) by solid-liquid separation treatment, and a sample solution containing the particles for separation and recovery is prepared.

There are no particular limitations on the method used for solid-liquid separation treatment provided is allows particles for separation and recovery suspended in the solution to be recovered by separating liquid and solid components, and a method can be used by suitably selecting from among known processes used for solid-liquid separation treatment. For example, centrifugal separation may be carried out on a solution containing a tripartite complex to precipitate the particles for separation and recovery followed by removing the supernatant, filtering the solution using filter paper or a filtration filter, and recovering the particles for separation and recovery remaining on the surface of the filter paper and the like. In addition, in the case the particles for separation and recovery are magnetic particles, a magnet may be brought in close proximity to a container containing the solution followed by causing the particles for separation and recovery to converge at the surface of the container in closest proximity to the magnet, and removing the supernatant.

The sample solution is prepared by suspending the recovered particles for separation and recovery in a suitable solvent. There are no particular limitations on the solvent provided it is a solvent that does not inhibit detection of light released from a luminescent probe bound to a target particle or inhibit detection of a luminescent probe bound to a target particle according to the scanning molecule counting method, and a solvent can be used by suitably selecting from among buffers commonly used in the relevant technical field. Examples of these buffers include phosphate buffers or Tris buffers such as phosphate-buffered saline (PBS, pH 7.4).

The recovered particles for separation and recovery may be washed with buffer prior to preparing the sample solution. Washing makes it possible to more precisely separate and remove free luminescent probe from the particles for separation and recovery.

Subsequently, in the (c), the number of the tripartite complex present in the prepared sample solution (number of target particles bound to luminescent probe) is counted according to the scanning molecule counting method. More specifically, the number of the tripartite complex is calculated by placing the sample solution in the aforementioned optical analysis device for use with the scanning molecule counting method, and detecting and analyzing light released from the luminescent probe in the tripartite complex using the aforementioned technique. The calculated number of molecules of the tripartite complex is the number of target particles in the sample solution.

The tripartite complex containing particles for separation and recovery is a large particle, and its diffusion movement speed in solution is comparatively slow. Consequently, in the case of measuring the sample solution according to the scanning molecule counting method in the (c), in addition to movement of the location of the photodetection region being such that the location of the photodetection region in the sample solution is moved along a prescribed scanning track, the scanning track may be moved so that the location of the photodetection region does not pass the same region as much as possible within a short period of time (excluding path intersections). Namely, the location of the photodetection region is moved along a second path on which the location thereof moves along a first path in the sample solution. Since the photodetection region scans different regions in the sample solution, excluding path intersections, during the movement of its location, the possibility of the same tripartite complex being detected as a different particle is reduced considerably, and variations in the number of detections of a tripartite complex are reduced, or effects attributable to discoloration of the luminescent probe in the tripartite complex are held to a minimum.

EXAMPLES

Although the following provides a more detailed explanation of the present invention by indicating examples and the like thereof, the present invention is not limited to the following examples.

Example 1

ATTO™ 488-biotin present in a solution was detected according to the method for detecting a target particle of the present embodiment by using ATTO™ 488 as luminescent probe, using ATTO™ 488-biotin as target particles labeled with the luminescent probe, and using magnetic particles as particles for separation and recovery.

More specifically, ATTO™ 488-biotin (Sigma-Aldrich Corp.) and ATTO™ 488 (Atto-Tec GmbH) were respectively dissolved to a concentration of 0.2 μM using TE buffer containing 1 M NaCl and 0.05% by volume (v/v) Pluoronic F-127 (to be referred to as "buffer" in the present example). A solution obtained by mixing ATTO™ 488-biotin and ATTO™ 488 at a volume ratio of 0:1000, 1:999, 5:995 or 10:990 was used as a 0% (mol), 0.1% (mol), 0.5% (mol) or 1.0% (mol) dye-modified biotin solution, respectively. Next, 25 μL of 10 mg/mL (approx. 10 pM) streptavidin-modified magnetic beads (trade name: Dynabeads™ MyOne Streptavidin C1, Invitrogen Corp.) and 25 μL of dye-modified biotin solution were mixed to prepare a suspension. The biotin in the ATTO™ 488-biotin was bound to the streptavidin on the magnetic beads by incubating each suspension for 30 minutes.

The magnetic beads in each suspension were precipitated using a magnet followed by removal of all of the supernatant. After re-suspending the remaining magnetic beads by adding 1 mL of buffer, the magnetic beads were precipitated using a magnet followed by removal of the supernatant. This same procedure was repeated a total of six times to wash the magnetic beads. After washing, the magnetic beads were suspended in 25 μL of buffer to prepare a (purified) suspension.

The number of ATTO™ 488-biotin bound to streptavidin-modified magnetic beads in each of the resulting (purified) suspensions was counted according to the scanning molecule counting method. Each of the suspensions that had not undergone purification treatment using a magnet (non-purified) was also similarly counted according to the scanning molecule counting method as a control.

More specifically, solutions obtained by diluting each of the aforementioned suspensions 1000-fold were used as sample solutions, and time series light intensity data (photon count data) was acquired for each sample solution using the MF-20 Single Molecule Fluorescence Spectroscopy System (Olympus Corp.) equipped with a confocal fluorescent microscope optical system and photon counting system. At that time, chronological light intensity data was generated by using 200 μW, 488 nm laser light as excitation light and measuring light in the wavelength band of 510 nm to 560 nm using a band pass filter. The photodetection region in the sample solutions was rotated at a movement speed of 15 mm/sec (6000 rpm), bin time was set to 10 μs, and measurement time was set to 2 seconds or 240 seconds. After smoothing the chronological light intensity data obtained from measurement, peaks were detected by differentiation. Those regions considered to be peaks that were able to be approximated with a Gaussian function were extracted as peak intensities having an intensity of 5 or more.

Figure 8:
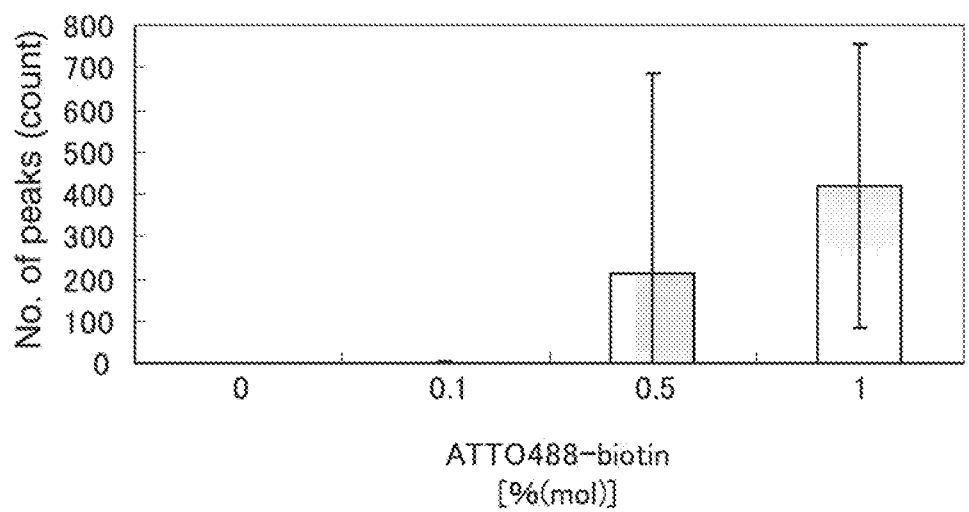
FIG. 8 is a drawing showing results for numbers of peaks obtained by measuring sample solutions subjected to purification treatment using a magnet according to a scanning molecule counting method in Example 1 using a measurement time of 240 seconds.
Figure 9:
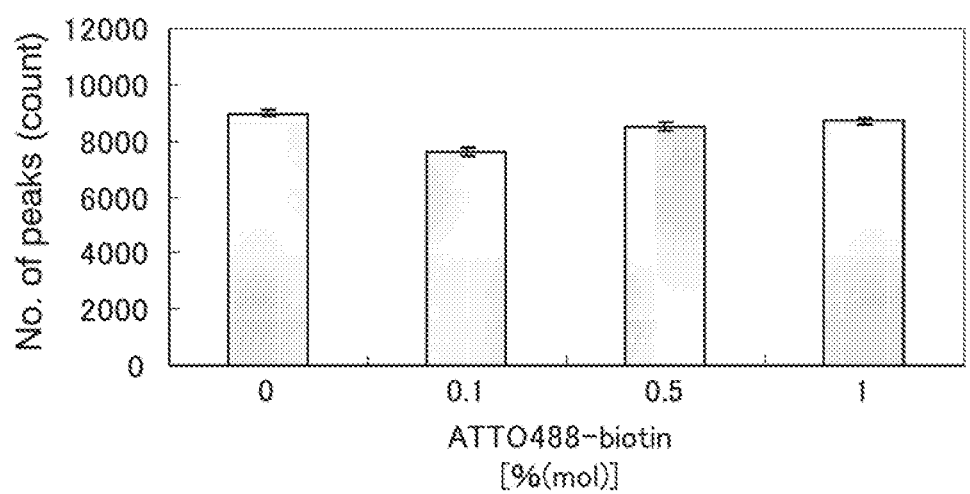
FIG. 9 is a drawing showing results for numbers of peaks obtained by measuring sample solutions subjected to purification treatment using a magnet according to a scanning molecule counting method in Example 1 using a measurement time of 2 seconds.

The results of counting according to the scanning molecule counting method are shown in FIGS. 8 and 9. FIG. 8 shows the results of measuring the sample solutions that underwent purification treatment using a magnet for a measurement time of 240 seconds, while FIG. 9 shows the results of measuring the sample solutions that did not undergo purification treatment using a magnet for a measurement time of 2 seconds. As a result, in the case of having carried out purification treatment, in contrast to hardly any peaks being detected for the 0% by volume dye-modified biotin solution, the number of peaks was observed to increase dependent on the amount of ATTO™ 488-biotin added (see FIG. 8). In contrast, in the case of not carrying out purification treatment, differences in the number of detected peaks were unable to be confirmed irrespective of the amount of ATTO™ 488-biotin added (see FIG. 9). On the basis of these results, the detection accuracy of target particles was demonstrated to be improved by purifying target particles bound to a luminescent probe using magnetic particles and removing excess luminescent probe not bound to the target particles.

Example 2

The sample solutions prepared in Example 1 were measured according to the scanning molecule counting method using a system for moving the location of the sample solution by moving the location of the photodetection region along a second path on which the location moves along a first path within a plane within the sample solution.

More specifically, each of the sample solutions used for measuring according to the scanning molecule counting method in Example 1 was measured according to the scanning molecule counting method under the conditions indicated below using the MF-20 Single Molecule Fluorescence Spectroscopy System used in Example 1. Chronological light intensity data was generated by using 200 μW, 488 nm laser light as excitation light and measuring light in the wavelength band of 510 nm to 560 nm using a band pass filter. The photodetection region in the sample solutions was rotated at a movement speed of 15 mm/sec (6000 rpm). The measurement container driven at 1 mm/s in a circle (OD: 1 mm). In addition, bin time was set to 10 μs, and measurement time was set to 2 seconds or 240 seconds. After smoothing the chronological light intensity data obtained from measurement, peaks were detected by differentiation. Those regions considered to be peaks that were able to be approximated with a Gaussian function were extracted as peak intensities having an intensity of 5 or more.

Figure 10:
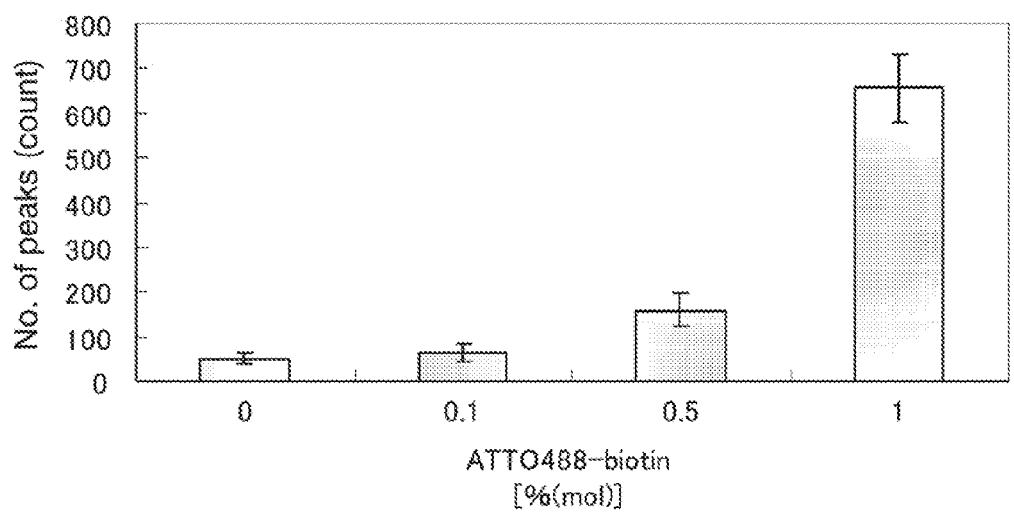
FIG. 10 is a drawing showing results for numbers of peaks obtained by measuring sample solutions subjected to purification treatment using a magnet according to a scanning molecule counting method in Example 2 using a measurement time of 240 seconds.
Figure 11:
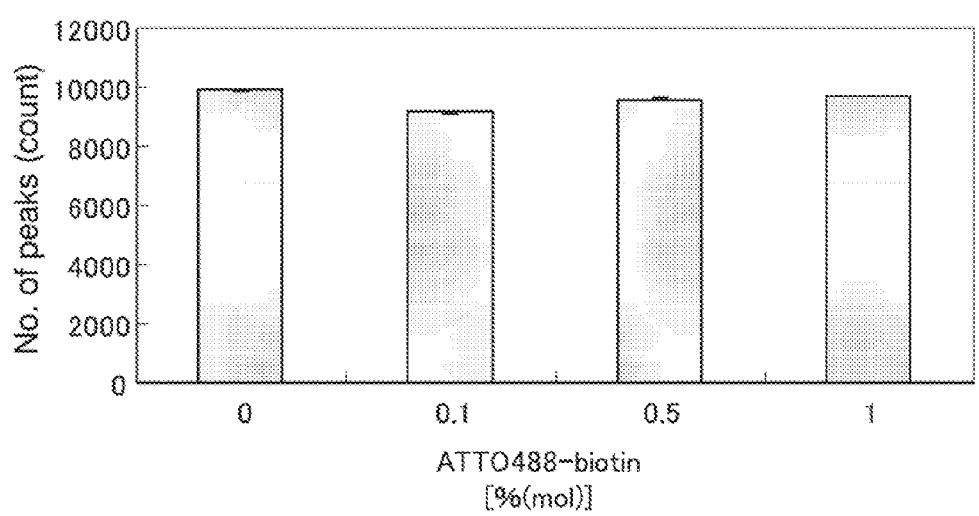
FIG. 11 is a drawing showing results for numbers of peaks obtained by measuring sample solutions, not subjected to purification treatment using a magnet, according to a scanning molecule counting method in Example 2 using a measurement time of 2 seconds.

The results of counting according to the scanning molecule counting method are shown in FIGS. 10 and 11. FIG. 10 shows the results of measuring the sample solutions that underwent purification treatment using a magnet for a measurement time of 240 seconds, while FIG. 11 shows the results of measuring the sample solutions that did not undergo purification treatment using a magnet for a measurement time of 2 seconds. As a result, similar to Example 1, in the case of having carried out purification treatment, the number of peaks was observed to increase dependent on the amount of ATTO™ 488-biotin added (see FIG. 10). In contrast, in the case of not carrying out purification treatment, differences in the number of detected peaks were unable to be confirmed irrespective of the amount of ATTO™ 488-biotin added (see FIG. 11). In addition, in the case of having carried out purification treatment, standard deviation was smaller in comparison with the case of Example 1, thereby indicating that driving the stage makes it possible to reduce variations in measurement.

In the scanning molecule counting method used in the method for detecting a target particle according to the examples of the present invention, statistical processing involving the determination of fluctuations in fluorescence intensity is not carried out. Thus, according to the method for detecting a target particle of the examples of the present invention, target particles in a sample can be detected even in cases in which the target particles to be analyzed are only present in the sample in an extremely small amount. Moreover, in the method for detecting a target particle according to the examples of the present invention, measurement is carried out according to a scanning molecule counting method using a particle for separation and recovery after having separated and removed free luminescent probe not bound to the target particle from luminescent probe bound to the target particle. Consequently, detection of light from the free luminescent probe is effectively inhibited and the target particle can be detected with high accuracy.

BRIEF DESCRIPTION OF THE REFERENCE SYMBOLS

1 Optical analysis device (confocal microscope)
2 Light source
3 Single-mode optic fiber
4 Collimator lens
5 Dichroic mirror
6, 7, 11 Reflecting mirror
8 Object lens
9 Microplate
10 Well (sample solution container)
12 Condenser lens
13 Pinhole
14 Barrier filter
14a Dichroic mirror or polarizing beam splitter
15 Multi-mode optic fiber 16 Photodetector
17 Mirror light deflector
17a Stage position adjustment device
18 Computer

The invention claimed is:

1. A method for detecting a target particle, comprising:
(a) preparing a pre-separation solution containing a target particle, a luminescent probe that binds to the target particle, and a particle for separation and recovery that is capable of being bound to a complex composed of the target particle and the luminescent probe, or containing the target particle bound to the luminescent probe, the luminescent probe and the particle for separation and recovery, and forming a complex comprising the target particle, the luminescent probe and the particle for separation and recovery in the solution,
(b) recovering the particle for separation and recovery from the pre-separation solution by solid-liquid separation treatment after (a), and preparing a sample solution containing the particles for separation and recovery, and
(c) calculating the number of the complex comprising the target particle, the luminescent probe and the particle for separation and recovery present in the sample solution prepared in (b), thereby detecting the target particle;
wherein the particle for separation and recovery binds to the complex composed of the target particle and the luminescent probe in (a),
wherein the calculating of the number of the complex comprising the target particle, the luminescent probe and the particle for separation and recovery in (c) is carried out by:
detecting light released from the complex comprising the target particle, the luminescent probe and the particle for separation and recovery in a photodetection region, while moving the location of the photodetection region of an optical system in the sample solution at a speed faster than the diffusion movement speed of the complex comprising the target particle, the luminescent probe and the particle for separation and recovery, using the optical system of a confocal microscope or multi-photon microscope, thereby obtaining a chronological light intensity data of the sample solution,
smoothing the chronological light intensity data,
individually detecting the complex comprising the target particle, the luminescent probe and the particle for separation and recovery from the detected light by individually detecting optical signals from individual complexes comprising the target particle, the luminescent probe and the particle for separation and recovery dispersed and randomly moving in the sample solution, based on a shape of smoothed chronological light intensity data, and
counting the number of target particles detected during movement of the location of the photodetection region by counting the number of individually detected complexes comprising the target particle, the luminescent probe and the particle for separation and recovery.

2. The method for detecting a target particle according to claim 1, wherein the sedimentation rate of the particles for separation and recovery in the sample solution is $1\times10^{-6}$ m/s or less.

3. The method for detecting a target particle according to claim 1, wherein, in the moving of the location of the photodetection region, the location of the photodetection region is moved along a second path over which the location thereof moves along a first path.

4. The method for detecting a target particle according to claim 3, wherein the first and second paths are circulation paths, and a movement cycle of the location of the photodetection region along the second path is shorter than the movement cycle of the location of the second path along the first path.

5. The method for detecting a target particle according to claim 3, wherein a movement cycle $\tau1$ of the location of the photodetection region, a movement speed $v2$ of the location of the second path, and a diameter d of the photodetection region satisfy the following relational expression:

$$v2\cdot\tau1>d.$$

6. The method for detecting a target particle according to claim 3, wherein the location of the photodetection region moves along the second path by changing the light path of the optical system, and the location of the second path in the sample solution moves along the first path by moving the location of the sample solution.

7. The method for detecting a target particle according to claim 3, wherein the second path is circular or elliptical, and the first path is circular, elliptical or linear.

8. The method for detecting a target particle according to claim 1, wherein, in the individually detecting of the complex comprising the target particle, the luminescent probe and the particle for separation and recovery by individually detecting optical signals from individual complexes comprising the target particle, the luminescent probe and the particle for separation and recovery from the detected light, the entry of a single complex comprising the target particle, the luminescent probe and the particle for separation and recovery into the photodetection region is detected based on the form of a chronologically detected light signal.

9. The method for detecting a target particle according to claim 1, wherein the particle for separation and recovery is a magnetic particle.

* * * * *